United States Patent [19]

Varney et al.

[11] Patent Number: 5,981,748

[45] Date of Patent: Nov. 9, 1999

[54] SYNTHESIS OF OPTICALLY PURE COMPOUNDS USEFUL AS GARFT INHIBITORS AND THEIR INTERMEDIATES

[75] Inventors: Michael D. Varney, Calsbad; William H. Romines, San Diego; Cynthia L. Palmer, La Mesa, all of Calif.

[73] Assignee: Agouron Pharmaceuticals, Inc., La Jolla, Calif.

[21] Appl. No.: 09/109,056

[22] Filed: Jul. 2, 1998

Related U.S. Application Data

[62] Division of application No. 08/472,233, Jun. 7, 1995, Pat. No. 5,831,100.

[51] Int. Cl.$^6$ .................... C07D 513/00; C07D 333/22; C07D 333/38

[52] U.S. Cl. ................. 544/48; 549/70; 549/71; 549/72

[58] Field of Search ............... 549/70, 71, 72; 544/48

[56] References Cited

U.S. PATENT DOCUMENTS

| | | | |
|---|---|---|---|
| 4,123,550 | 10/1978 | Untch et al. | 424/275 |
| 4,684,653 | 8/1987 | Taylor et al. | 514/258 |
| 4,686,223 | 8/1987 | Cohnen et al. | 514/272 |
| 4,831,037 | 5/1989 | Taylor et al. | 514/258 |
| 4,845,216 | 7/1989 | Taylor et al. | 514/272 |
| 4,871,743 | 10/1989 | Taylor et al. | 514/250 |
| 4,871,746 | 10/1989 | Taylor et al. | 514/279 |
| 4,880,812 | 11/1989 | Kelley | 514/272 |
| 4,882,333 | 11/1989 | Shih et al. | 514/258 |
| 4,882,334 | 11/1989 | Shih et al. | 514/258 |
| 4,883,799 | 11/1989 | Taylor et al. | 514/258 |
| 4,889,859 | 12/1989 | Taylor et al. | 514/272 |
| 4,895,946 | 1/1990 | Taylor et al. | 514/272 |
| 4,920,125 | 4/1990 | Taylor et al. | 514/279 |
| 4,921,836 | 5/1990 | Bigham et al. | 514/272 |
| 4,927,828 | 5/1990 | Taylor et al. | 514/258 |
| 4,971,973 | 11/1990 | Bigham et al. | 514/272 |
| 4,973,715 | 11/1990 | Roux et al. | 549/502 |
| 4,988,813 | 1/1991 | Taylor et al. | 514/258 |
| 5,013,738 | 5/1991 | Taylor et al. | 514/258 |
| 5,015,656 | 5/1991 | Fernandez et al. | 514/422 |
| 5,026,851 | 6/1991 | Taylor et al. | 514/258 |
| 5,034,049 | 7/1991 | Kober et al. | 71/90 |
| 5,179,123 | 1/1993 | Djuric et al. | 514/461 |
| 5,217,974 | 6/1993 | Grindey et al. | 514/260 |
| 5,223,503 | 6/1993 | Gossett et al. | 514/258 |
| 5,594,139 | 1/1997 | Varney et al. | 544/48 |
| 5,608,082 | 3/1997 | Varney et al. | 549/70 |
| 5,831,100 | 11/1998 | Varney et al. | 549/70 |

(List continued on next page.)

FOREIGN PATENT DOCUMENTS

| | | |
|---|---|---|
| 2678377 | 5/1988 | European Pat. Off. . |
| 325343 | 7/1989 | European Pat. Off. . |
| 341837 | 11/1989 | European Pat. Off. . |
| 438261 | 7/1991 | European Pat. Off. . |
| 593286 | 4/1994 | European Pat. Off. . |
| WO 86/05181 | 9/1986 | WIPO . |
| WO 92/05153 | 4/1992 | WIPO . |
| WO 94/13295 | 6/1994 | WIPO . |
| WO 94/17076 | 8/1994 | WIPO . |
| WO 96/03406 | 2/1996 | WIPO . |
| WO 96/03407 | 2/1996 | WIPO . |

OTHER PUBLICATIONS

Moran, "Folate antimetabolites inhibitory to de novo purine synthesis," New Drugs, Concepts and Results in Cancer Chemotherapy, (Muggia ed.), Kluwer Academic Publishers, Boston (1992), 65–87.

Young et al., "An Antibody Probe to Determine the Native Species of Glycinamide Ribonucleotide Transformylase in Chicken Liver," Biochemistry, vol. 23, No. 17 (1984), 3979–3986.

Morrison, "Kinetics of the Reversible Inhibition of Enzyme– atalysed Reactions by Tight–Binding Inhibitors," Biochem. Biophys. Acta, vol. 185 (1963), 269–286.

(List continued on next page.)

*Primary Examiner*—Deborah C. Lambkin
*Attorney, Agent, or Firm*—Finnegan, Henderson, Farabow, Garrett & Dunner, L.L.P.

[57] ABSTRACT

The invention relates to methods of making compounds of the formula VII

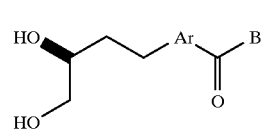

and their enantiomers, where Ar is a substituted or unsubstituted five- or six-membered aromatic group and B is either an amino acid linked through the amino portion to form an amide or a $C_1$–$C_6$ alcohol linked through the alcohol portion to form an ester. These compounds are advantageously employed as intermediates to prepare optically pure compounds that are active GARFT inhibitors. In one method, a compound of the formula

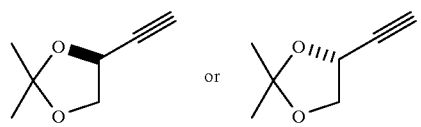

is reacted with a compound of the formula

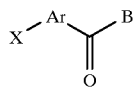

where X is a halogen.

13 Claims, No Drawings

OTHER PUBLICATIONS

Totani et al., "Synthesis of a Novel 5–Deaza–5–thia Analogue of Tetrahydrofolic Acid . . . ," J. Chem. Soc. Perkin Trans. 1 (Apr. 1994), 833–836.

Mosmann, "Rapid Colorimetric Assay for Cellular Growth and Survival . . . ," J. Immunol. Methods, vol. 65 (1983), 55–63.

Sako et al., "New and Facile Synthesis of 5,6,7, 8–Tetrahydro–5–deaza–5–thiapterins . . . ," Chem. Pharm. Bull., vol. 42, No. 4 (1994), 806–810.

Antony, "The Biological Chemistry of Folate Receptors," Blood—The Journal of the American Society of Hematology, vol. 79, No. 11 (1992), 2807–2820.

Pizzorno et al., "5,10–Dideazatetrahydrofolic Acid (DDATHF) Transport in CCRF–CEM and MA104 Cell Lines," The Journal of Biological Chemistry, vol. 268, No. 2 (1993), 1017–1023.

Alati et al., "Evaluation of the Mechanism(s) of Inhibition of the Toxicity, But Not the Antitumor Activity of Lometrexol . . . ," Proceedings of the Am. Assoc. for Cancer Res., Abstract 2432, vol. 33 (1992), 407.

Shih et al., "Synthesis and Biological Activity of Acyclic Analogues of 5,10–Dideaza–5,6,7,8–tetrahydrofolic Acid," J. Med. Chem., vol. 35 (1992), 1109–1116.

Nemec et al., "The Synthesis of 4–Substituted 2–Thiophenecarboxylic Acids," Collection Czechoslov. Chem. Commun., vol. 39 (1974), 3527–3531.

Taylor et al., "Convergent and Efficient Palladium–Effected Synthesis of . . . (DDATHF)," J. Org. Chem., vol. 54, No. 15 (1989), 3618–3624.

Habeck et al., "A Novel Class of Monoglutamated Antifolates Exhibits Tight–binding Inhibition of Human Glycinamide Ribonucleotide Formyltransferase and Potent Activity Against Solid Tumors," Cancer Research, vol. 54 (Feb. 15, 1994), 1021–1026.

Henrie II et al., "Preparation of 2–Amino–4(3H)–oxopyrimido[5,4–b][1,4]–thiazines . . . ," J. Med. Chem., vol. 26, No. 4 (1993), 559–563.

Okafar, "Studies in the Heterocyclic Series XVIII . . . ," J. Heterocyclic Chem., vol. 17 (1980), 1587–1592.

Alley et al., "Feasibility of Drug Screening with Panels of Human Tumor Cell Lines Using Microculture Tetrazolium Assay," Cancer Res., vol. 48 (1988), 589–601.

Cleland, "The Kinetics of Enzyme–Catalyzed Reactions with Two or More Substrates or Products," Biochem. Biophys. Acta, vol. 67 (1963), 173–187.

Casarrubio et al., "On the Syntheses of Thiophene Analogs of Practolol and 'Reversed' Practolol," J. Heterocyclic Chem., vol. 20 (Nov.–Dec. 1983), 1557–1560.

Kisliuk et al., Chemical Abstracts, vol. 113, No. 9, Abstract No. 70792k (1990).

Sako et al., "First Synthesis of 5,6,7, 8–Tetrahydro–8–deaza–thiafolic Acid," Chem. Pharm. Bull., vol. 40, No. 1 (1992), 49–52.

Taylor et al., "Studies on the Molybdenum Cofactor. Determination of the Structure and Absolute Configuration of Form A," J. Am. Chem. Soc., vol. 111, No. 19 (1989), 7664–7665.

SYNTHESIS OF OPTICALLY PURE COMPOUNDS USEFUL AS GARFT INHIBITORS AND THEIR INTERMEDIATES

This application is a division of U.S. patent application Ser. No. 08/472,233, filed Jun. 7, 1995 U.S. Pat. No. 5,831,100. This patent application is entirely incorporated herein by reference.

FIELD OF INVENTION

The present invention relates to methods of making optically pure compounds that inhibit the enzyme glycinamide ribonucleotide formyl transferase (GARFT). The invention also relates to the optically pure intermediates useful for making the optically pure GARFT-inhibiting compounds and to the syntheses of these intermediates.

BACKGROUND OF INVENTION

GARFT is a folate-dependent enzyme in the de novo purine biosynthesis pathway. This pathway is critical to cell division and proliferation. Shutting down this pathway is known to have an antiproliferative effect, in particular, an antitumor effect. Compounds that inhibit GARFT consequently inhibit the growth and proliferation of the cells of higher organisms or microorganisms such as bacteria, yeast and fungi.

A number of folate analogs have been synthesized and studied for their ability to inhibit GARFT. A prototypical specific tight-binding inhibitor of GARFT, 5,10-dideazatetrahydrofolic acid, has been reported to show antitumor activity. See F. M. Muggia, "Folate antimetabolites inhibitor to de novo purine synthesis," *New Drugs, Concepts and Results in Cancer Chemotherapy,* Kluwer Academic Publishers, Boston (1992), 65–87.

Antifolates or antifoles are a subclass of antiproliferative antimetabolites and are antagonists of the vitamin folic acid. Typically, antifolates closely resemble the structure of folic acid and incorporate the characteristic P-benzoyl glutamate moiety of folic acid. The glutamate moiety of folic acid takes on a double negative charge at physiological pH. Thus, this compound and its analogs have an active energy-driven transport system to cross the cell membrane and exert a metabolic effect.

Compounds useful as antiproliferative agents or GARFT inhibitors, such as certain glutamic acid derivatives, have been recently developed as described in U.S. application Ser. No. 08/282,293 to Varney et al., filed Jul. 28, 1994, and in International Application PCT/US94/00418 to Varney et al., filed on Jan. 18, 1994, the disclosures of which are herein incorporated by reference. Such compounds also have antitumor, antiinflammatory, antipsoriatic and/or immunosuppressive activity. The present invention relates to advantageous methods of making such compounds in optically pure forms in good yields. The invention also relates to optically pure intermediates useful for making the antiproliferative agents/GARFT inhibitors and to methods of making these intermediates.

SUMMARY OF INVENTION

In light of the pharmacological activity of GARFT-inhibiting or antiproliferative compounds, it would be desirable to develop a method for conveniently preparing such compounds in optically pure forms. As generally understood by those skilled in the art, an optically pure compound having one chiral center (i.e., one asymmetric carbon atom) is one that consists primarily of one of the two possible enantiomers (i.e., is enantiomerically pure), and an optically pure compound having more than one chiral center is one that is diastereomerically pure. As used herein, the term "optically pure" is intended to mean a compound which consists of at least a sufficient amount of a single enantiomer (or diastereomer in the case of plural chiral centers) to yield a compound having the desired pharmacological activity. Preferably, "optically pure" is intended to mean a compound that consists of at least 90% of a single isomer (80% enantiomeric or diastereomeric excess), preferably at least 95% (90% e.e. or d.e.), more preferably at least 97.5t (95% e.e. or d.e.), and most preferably at least 99% (98% e.e. or d.e.).

An object of the present invention is to develop methods for preparing in good yields GARFT-inhibiting, antiproliferative compounds in optically pure forms. More specifically, an object of the invention is to develop a method for synthesizing optically pure compounds of formula

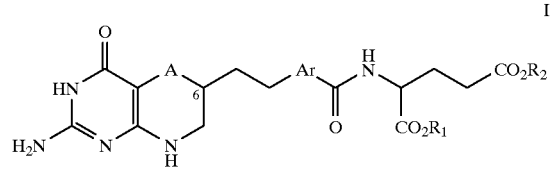

I where A is an oxygen, sulfur or selenium atom, Ar is a substituted or unsubstituted five- or six-membered aromatic group, and $R_1$ and $R_2$ are independently a hydrogen atom or a moiety that forms together with the attached $CO_2$ a readily hydrolyzable ester group. Additional objects and advantages of the invention will be apparent from the detailed description, which follows.

The objects of the invention have been achieved by a method of preparing optically pure compounds of formula I

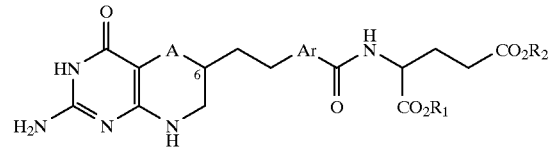

by reacting a compound of formula

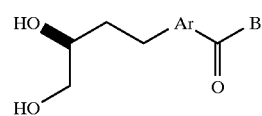

VII or its enantiomer
where Ar is a substituted or unsubstituted five- or six-membered aromatic group and B is either an amino acid linked through the amino portion to form an amide or a $C_1$–$C_6$ alcohol linked through the alcohol portion to form an ester, under conditions suitable to form a compound of formula I that is optically pure.

The diol compounds of formula VII and their enantiomers are optically pure intermediates useful for making the optically pure GARFT inhibitors and antiproliferative agents. In formula VII, preferably Ar is a 5-membered aromatic group having a sulfur ring atom. A preferred amino acid for B is diethyl glutamate, and a preferred $C_1$–$C_6$ alcohol for a is methanol or ethanol. A preferred intermediate is 5-(3(S)-4-dihydroxy-butyl)-thiophene-2-carboxylic acid ethyl ester.

Intermediate compounds of formula VII and their enantiomers are advantageously prepared in accordance with the invention by a method comprising:

(a) reacting a compound of the formula III

III or its enantiomer

XVII with a compound of the formula IV

IV where X is bromo, fluoro, chloro or iodo, and B and Ar are as defined above,
to form a compound of the formula V

V where Ar and B are as defined above, or its enantiomer;

(b) reacting the compound of formula V or its enantiomer with a reducing agent to obtain a compound of formula VI

VI where Ar and B are as defined above, or its enantiomer; and (c) reacting the compound of formula VI or its enantiomer with an acid under conditions suitable to form the compound of formula VII or its enantiomer.

Preferably, in step (a) the reaction is carried out in the presence of (i) a transition-metal catalyst containing one or more metals selected from palladium, copper and nickel, and (ii) a non-nucleophilic auxiliary base (iii) in a solvent in which at least one of the reactant compounds is at least partially soluble; in step (b) the reducing agent is hydrogen gas in the presence of a metal catalyst containing palladium or platinum; and in step (c) the acid is p-toluenesulfonic acid.monohydrate and the reaction is carried out in methanol or ethanol.

Other features and advantages of the invention will be apparent from the following detailed description, which illustrates preferred embodiments of the invention.

DETAILED DESCRIPTION AND PREFERRED EMBODIMENTS OF INVENTION

As explained above, the invention relates generally to a method of making optically pure forms of antiproliferative compounds capable of inhibiting GARFT of formula I and their pharmaceutically acceptable salts:

I where:

A is an oxygen, sulfur or selenium atom;

Ar is a substituted or unsubstituted five- or six-membered aromatic group; and $R_1$ and $R_2$ are independently a hydrogen atom or a moiety that forms together with the attached $CO_2$ a readily hydrolyzable ester group. The carbon at position 6 shown in formula I is in either the pure R or the pure S configuration.

Preferably, $R_1$ and $R_2$ are independently selected from hydrogen, $C_1$–$C_6$ alkyl, hydroxyalkyl, alkylaryl and arylalkyl. More preferably, $R_1$ and $R_2$ are each hydrogen or a $C_1$–$C_2$ alkyl.

Preferably, A is sulfur.

Ar is preferably a five-membered aromatic group that is either substituted or unsubstituted. Illustrative examples of suitable substituents for the substituted species of Ar include alkyl groups such as methyl, ethyl and propyl, substituted alkyl groups, such as trifluoromethyl, and halogens, such as bromo and chloro.

Preferred compounds of formula I are those of the subgenus defined by formula II:

II where:

A' is sulfur or selenium;

Y is oxygen or sulfur;

C and D are independently hydrogen or a substituted or unsubstituted $C_1$–$C_6$ alkyl group; and $R_1$ and $R_2$ are independently hydrogen or a moiety that forms together with the attached $CO_2$ a readily hydrolyzable ester group. The C6 (asymmetric) carbon is in either the pure R or the pure S configuration.

Preferably, $R_1$ and $R_2$ are independently selected from hydrogen, $C_1$–$C_6$ alkyl, hydroxyalkyl, alkylaryl and arylalkyl. More preferably, these substituents are independently hydrogen or a $C_1$–$C_2$ alkyl. A is preferably sulfur. Preferably, Y is sulfur. In preferred embodiments, C is hydrogen or methyl, and D is hydrogen or methyl. Illustrative examples of suitable substituents for the substituted species of C and D include alkyl groups such as methyl and ethyl.

Although the compounds are depicted in formulae I and II in the 4-oxo form and are referred to as such throughout this description, the oxo group exists in tautomeric equilibrium with the corresponding 4-hydroxy group. It therefore will be understood that the tautomeric hydroxy forms are also intended to be covered by the formulae.

The compounds of formulae I and II in which $R_1$ and R2 are hydrogen are active antitumor and antiproliferative compounds. The compounds where $R_1$ and $R_2$ are each a moiety, preferably an ethyl group, that forms with the attached $CO_2$ a readily hydrolyzable ester group, are intermediates for forming the free glutamic acid forms of the compounds and can also be hydrolyzed in vivo and thus act as prodrugs.

The pharmaceutically acceptable salts of the compounds of formulae I and II include, e.g., non-toxic metal salts, such as alkaline metal and alkaline earth metal salts, and substituted and unsubstituted ammonium salts of the glutamic acid compounds of the above formulae. Exemplary salts include sodium, potassium, lithium, calcium, magnesium, and substituted and unsubstituted pyridinium salts.

The invention relates to methods of making both chiral forms (C6=asymmetric carbon atom) of compounds of formula I or II. In a preferred embodiment for making optically pure C6 (R) forms of the compounds of formula I or II, the following compound of formula III:

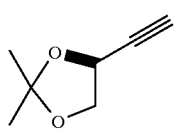

III is reacted under suitable conditions with a compound of formula IV:

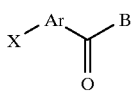

IV where X is a halogen (bromo, fluoro, chloro or iodo), preferably bromo; B is either an amino acid, preferably diethyl glutamate, linked through the amino portion to form an amide, or a $C_1$–$C_6$ alcohol, preferably methyl or ethyl alcohol, linked through the alcohol portion to form an ester; and Ar is as defined in formula I The compound of formula III may be prepared in accordance with methods known to the art, such as described in *J. Am. Chem. Soc.,* vol. 111 (1989), 7664–7665.

The reaction of the compounds of formulae III and IV is preferably carried out in the presence of (i) a suitable transition-metal catalyst, preferably palladium, copper, nickel or a mixture of two or more of these metals, and (ii) a non-nucleophilic auxiliary base, preferably a substituted amine (e.g., triethylamine or diethylamine), (iii) in a solvent in which at least one of the reactant compounds is at least partially soluble. The reaction is performed under conditions sufficient to obtain a compound of formula V:

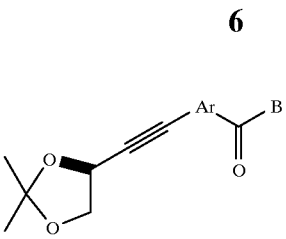

V where Ar is as defined in formula I and B is as defined in formula IV.

The compound of formula V is then reduced under suitable conditions to obtain a compound of the formula VI:

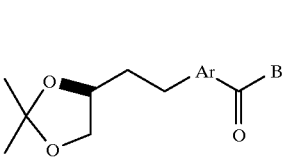

VI where Ar is as defined in formula I and B is as defined in formula IV. Preferably, the compound of formula V is reduced with hydrogen gas in the presence of a suitable metal catalyst, preferably palladium or platinum.

The compound of formula VI is reacted under conditions suitable to obtain an intermediate compound of formula VII:

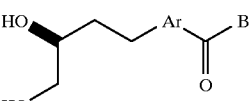

VII where Ar is as defined in formula I and B is as defined in formula IV. Preferably, the compound of formula VI is reacted with an acid, preferably p-toluenesulfonic acid.monohydrate, in an alcoholic solvent, preferably methanol or ethanol.

The compound of the formula VII is reacted with a sulfonylating agent, preferably p-toluenesulfonyl chloride or methanesulfonylchloride, in the presence of a non-nucleophilic base, preferably triethylamine or diisopropylethyl amine, to give an intermediate mono-sulfonylated compound. This intermediate is then reacted with a nitrogen nucleophile, preferably sodium azide, to obtain the compound of the formula VIII:

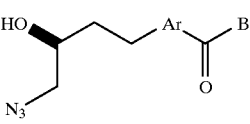

VIII where Ar is as defined in formula I and B is as defined in formula IV.

The azide functionality of the compound of formula VIII is reduced under suitable conditions, preferably hydrogen gas in the presence of a metal catalyst, and subsequently protected with a suitable nitrogen-protecting group, preferably t-butoxycarbonyl, benzyloxycarbonyl or benzyl, to provide a compound of formula IX:

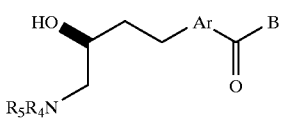

IX where Ar is as defined in formula I; B is as defined in formula IV; and $R_4$ and $R_5$ are independently hydrogen or a suitable nitrogen-protecting group that is readily removed in the presence of another sensitive functionality. Preferred nitrogen-protecting groups for $R_4$ and $R_5$ are t-butoxycarbonyl, benzyloxycarbonyl and benzyl.

The compound of formula IX is then reacted under conditions suitable to obtain a compound of the formula X:

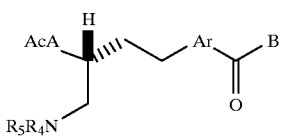

X where A and Ar are as defined in formula I; B is as defined in formula IV; $R_4$ and $R_5$ are as defined in formula IX; and Ac is an acyl group, preferably acetyl.

Preferably, the compound of formula IX is reacted with an acylating or sulfonylating agent, preferably methanesulfonyl chloride or p-toluenesulfonyl chloride, in the presence of a non-nucleophilic base, preferably triethylamine or diisopropylethylamine, in a suitable solvent in which at least one of the reactants is at least partially soluble, to obtain an activated hydroxy group. The activated hydroxy group is subsequently displaced with a suitable nucleophile, preferably a thioacid salt, more preferably potassium thioacetate, to obtain a compound of formula X. Alternatively, the compound of formula IX is conveniently converted to the compound of formula X using (i) triphenylphosphine, (ii) diethyl, diisopropyl or dimethyl azadicarboxylate, and (iii) an acidic nucleophile, preferably thioacetic acid, (iv) in a suitable solvent.

The compound of the formula X is reacted under conditions suitable to obtain a compound of formula XI:

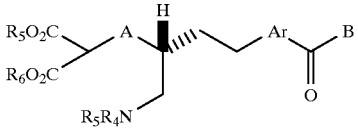

XI where A and Ar are as defined in formula I; B is as defined in formula IV; $R_4$ and $R_5$ are as defined in formula IX; and $R_6$ is hydrogen or a moiety that forms together with the attached $CO_2$ a readily hydrolyzable ester group, preferably $C_1$–$C_6$ alkyl, hydroxyalkyl, alkylaryl or aralkyl, more preferably a $C_1$–$C_2$ alkyl.

Preferably, the compound of formula X is treated with a nucleophilic base, preferably potassium carbonate, sodium carbonate, sodium hydroxide or potassium hydroxide, in an alcoholic solvent, preferably methanol, ethanol or isopropanol, in the presence of an alkylating agent, preferably dimethyl or diethyl chloromalonate, to obtain a compound of formula XI.

Alternatively, the compound of formula X is reacted with a nucleophilic base, preferably potassium carbonate, sodium carbonate, sodium hydroxide or potassium hydroxide, in an alcoholic solvent, preferably methanol, ethanol or isopropanol, to generate the oxidized dimer to obtain a compound of the formula XII:

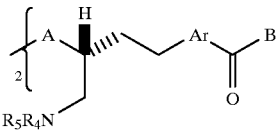

XII where A and Ar are as defined in formula I, B is as defined in formula IV, and $R_4$ and $R_5$ are as defined in formula IX. The compound of formula XII is then reacted with a reducing agent, preferably sodium borohydride, in an alcoholic solvent, preferably methanol or ethanol. The reduced product is then alkylated with a suitable alkylating agent, preferably diethyl or dimethyl chloromalonate, in the presence of a non-nucleophilic base, preferably sodium or potassium carbonate, to obtain the compound of formula XI.

The compound of the formula XI is then treated to remove either or both of the $R_4$ and $R_5$ protecting groups. For example, where a protecting group is t-butoxycarbonyl, the compound may be treated with trifluoroacetic acid and then neutralized to obtain a compound of the formula XIII:

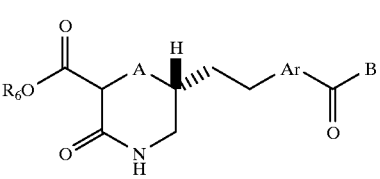

XIII where A and Ar are as defined in formula I, B is as defined in formula IV, and $R_6$ is as defined in formula XI.

The compound of formula XIII is then converted under suitable conditions to a compound of formula XIV:

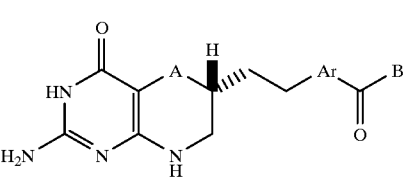

XIV where A and Ar are as defined in formula I, and B is as defined in formula IV.

Preferably, the compound of formula XIII is reacted with an alkylating agent, preferably trimethyl or triethyl oxonium tetrafluoroborate, in a suitable solvent, preferably dichloromethane, to form an intermediate lactim ether. The intermediate lactim ether is then reacted with guanidine in an alcoholic solvent, preferably methanol, ethanol or isopropanol, to form a compound of formula XIV. Alternatively, the compound of the formula XIII can be converted to the compound of the formula XIV by reacting the compound of the formula XIII with a thiolating agent, preferably $P_2S_5$ or (2,4-bis(4-methoxyphenyl)-1,3-dithia-2,4-diphosphetane-2,4-disulfide), to form the thiolactam intermediate. The ether is then alkylated with an alkylating agent, preferably methyl iodide or trimethyl or triethyl oxonium tetrafluoroborate, and then with guanidine in an alcoholic solvent, preferably methanol, ethanol or isopropanol, to obtain the compound of the formula XIV.

When B is an alcohol function so that the group attached with B forms an ester group, the compound of the formula XIV may be hydrolyzed under basic conditions to form a compound of the formula XV:

XV where A and Ar are as defined in formula I.

The compound of the formula XV can be peptide-coupled by means well known to those skilled in the art with a glutamic acid diester hydrochloride to form a diester of the formula XVI:

XVI where A, Ar, $R_1$, and $R_2$ are as defined in formula I except that neither $R_1$ nor $R_2$ is hydrogen.

Finally, if desired, the compound of the formula XVI is hydrolyzed to the free glutamic acid form depicted in formula I (i.e., both $R_1$ and $R_2$ are H).

Two methods may be used to prepare optically pure C6 (S) forms of the compounds depicted by formula I. The first method begins with the compound of the formula XVII (*J. Am. Chem. Soc.*, vol. 111 (1989), 7664–7665):

XVII

This compound is the enantiomer of the compound of the formula III. The compound of the formula XVII is then used in a manner analogous to that described above employing the compound of the formula III and the remainder of the synthesis is as described above, yielding an enantiomer of the formula XVI.

The second method to prepare the C6 (S) forms of she compounds of the formulae I and II employs the compound of formula VII. The compound of formula VII is reacted with a suitable protecting group, preferably a silylating agent, more preferably t-butyldimethylsilyl chloride, in the presence of a non-nucleophilic base, preferably triethylamine, in a suitable solvent, preferably dichloromethane, to obtain a compound of the formula XVIII:

XVIII where Ar is as defined in formula I, B is as defined in formula IV, and $R_7$ is a suitable hydroxy-protecting group, preferably t-butyldimethylsilyl.

The compound of formula XVIII is reacted with an acylating or sulfonylating agent, preferably methanesulfonyl chloride, to obtain a compound of formula XIX:

XIX

In formula XIX, Ar is as defined in formula I, B is as defined in formula IV, $R_7$ is as defined in formula XVIII, and $R_8$ is an acyl or sulfonyl group, preferably methanesulfonyl.

The compound of formula XIX is reacted with a reagent suitable to remove the protecting group $R_7$ and form an alcohol. Where $R_7$ is a silyl group, a preferred reagent is a fluoride salt, preferably tetrabutylammonium fluoride. The resulting alcohol is then treated with a strong non-nucleophilic base, preferably sodium or potassium hydride, to obtain a compound of formula XX:

XX where Ar is as defined in formula I, and B is as defined in formula IV.

The compound of formula XX is reacted with a nitrogen-containing anion, preferably sodium azide, in the presence of a Lewis acid, preferably lithium or magnesium perchlorate, in a suitable solvent, preferably acetonitrile, to obtain a compound of formula XXI:

XXI where Ar is as defined in formula I, and B is as defined in formula IV.

The compound of formula XXI is the enantiomer of the compound of formula VIII. The compound of formula XXI is processed in a manner analogous to that described above for the compound of formula VIII to prepare the compounds of the formula I having the C6 (S) configuration.

Exemplary compounds of the formula I made in accordance with the invention include: (2-(5-[2-(2-amino-4-oxo-4,6,7,8-tetrahydro-3H-pyrimido[5,4-6][1,4]thiazin-6(R)-yl)-ethyl]-thiophene)-2-L-glutamic acid) diethyl ester; (2-(5-[2-(2-amino-4-oxo-4,6,7,8-tetrahydro-3H-pyrimido[5,4-6][1,4]thiazin-6(S)-yl)-ethyl]-thiophene)-2-L-glutamic acid) diethyl ester; 2-(5-[2-(2-amino-4-oxo-4,6,7,8- tetrahydro-3H-pyrimido[5,4-6][1,4]thiazin-6(R)-yl)-ethyl]-thiophene)-2-L-glutamic acid; 2-(5-[2-(2-amino-4-oxo-4,6,7,8-tetrahydro-3H-pyrimido-[5,4-6][1,4]thiazin-6(S)-yl)-ethyl)-thiophene)-2-L-glutamic acid; (2-(5-[2-(2-amino-4-oxo-4,6,7,8-tetrahydro-3H-pyrimido-[5,4-6][1,4]thiazin-6 (R)-yl)-ethyl]-4-methylthiophene)-2-L-glutamic acid) diethyl ester; (2-(5-[2-(2-amino-4-oxo- 4,6,7,8-tetrahydro-3H-pyrimido[5,4-6][1,4]thiazin-6(S)-yl)-ethyl]-4-methylthiophene)-2-L-glutamic acid) diethyl ester; 2-(5-(2-(2-amino-4-oxo-4,6,7,8-tetrahydro-3H-pyrimido[5,4-6]-[1,4]thiazin-6(R)-yl)-ethyl]-4-methylthiophene)-2-L-glutamic acid; 2-(5-[2-(2-amino-4-oxo-4,6,7,8-tetrahydro-3H-pyrimido[5,4-6][1,4]thiazin-6(S)-yl)-ethyl]-4-methylthiophene)-2-L-glutamic acid; (2-(5-[2-(2-amino-4-oxo-4,6,7,8-tetrahydro-3H-pyrimido[5,4-6][1,4]thiazin-6 (R)-yl)-ethyl]-3-methylthiophene)-2-L-glutamic acid) diethyl ester; (2-(5-[2-(2-amino-4-oxo-4,6,7,8-tetrahydro-3H-pyrimido-[5,4-6][1,4]thiazin-6(S)-yl)-ethyl]-3-methylthiophene)-2-L-glutamic acid) diethyl ester; 2-(5-[2-(2-amino-4-oxo-4,6,7,8-tetrahydro-3H-pyrimido[5,4-6][1,4]thiazin-6(R)-yl)-ethyl]-3-methylthiophene)-2-L-glutamic acid; and 2-(5-[2-(2-amino-4-oxo-4,6,7,8-tetrahydro-3H-pyrimido[5,4-6]-[1,4]thiazin-6(S)-yl)-ethyl]-3-methylthiophene)-2-L-glutamic acid.

The compounds of the formulae I and II and their salts are particularly useful in the treatment of mammalian hosts, such as human hosts, and in the treatment of avian hosts. These compounds produce any one or more of an antiproliferative, antibacterial, antiparasitic, antiviral, antipsoriatic, antiprotozoal, anticoccidial, antiinflammatory, immunosuppressive and antifungal effect. The compounds are especially useful in producing an antitumor effect in a vertebrate host harboring a tumor.

The compounds of the formulae I and II, as well as their pharmaceutically acceptable salts, may be incorporated into convenient dosage forms, such as capsules, tablets and injectable preparations. Such pharmaceutical preparations may be prepared following conventional techniques of the pharmaceutical chemist involving steps such as mixing, granulation and compressing when necessary for tablet forms, or mixing, filling and dissolving the ingredients as appropriate, to give the desired products for oral, parenteral, topical, intravaginal, intranasal, intrabronchial, intraocular, intraaural and rectal administration.

Solid or liquid pharmaceutically acceptable carriers, diluents or excipients may be employed in the pharmaceutical compositions. Solid carriers include starch, lactose, calcium sulphate dihydrate, terra alba, sucrose, talc, gelatin, agar, pectin, acacia, magnesium stearate and stearic acid. Liquid carriers include syrup, peanut oil, olive oil, saline solution and water. The carrier or diluent may include any prolonged-release material, such as glyceryl monostearate or glyceryl distearate, alone or with wax. When a liquid carrier is used, the preparation may be in the form of a syrup, elixir, emulsion, soft gelatin capsule, sterile injectable liquid (e.g. solution) or a nonaqueous or aqueous liquid suspension.

A dose of a composition contains at least an effective quantity of the active compound (i.e., a compound of the formula I or a pharmaceutically acceptable salt thereof) and preferably is made up of one or more pharmaceutical dosage units. An effective quantity is a quantity sufficient to inhibit the folate metabolic pathway and derive the beneficial effects therefrom, e.g., through administration of one or more of the pharmaceutical dosage units.

An exemplary daily dose for a vertebrate host contains an amount up to one gram of active compound per kilogram body weight of the host, preferably one-half of a gram, more preferably 100 milligrams, and even more preferably, about 50 milligrams or less, per kilogram of the host weight. The selected dose may be administered to a warmblooded animal or mammal, for example, a human patient in need of treatment mediated by folate metabolic pathway inhibition, by any known method of administrating the dose including: topically, for example, as an ointment or cream; orally; rectally, for example, as a suppository; parenterally by injection; or continuously by intravaginal, intranasal, intrabronchial, intraaural or intraocular infusion.

Preferred embodiments of the invention are described in the following examples, which are provided for illustrative purposes.

EXAMPLE 1

Preparation of 2-(5-[2-(2-Amino-4-oxo-4,6,7,8-tetrahydro-3H-pyrimido[5,4-6][1,4]thiazin-6(R)-yl)-ethyl]-thiophene)-2-L-glutamic acid (15)

(a) Preparation of 5-(2,2-Dimethyl-[1,3]dioxolan-4(S)-yl-ethynyl)-thiophene-2-carboxylic acid ethyl enter (1)

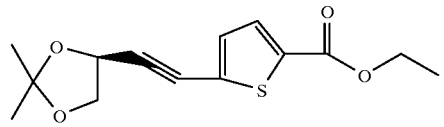

(1)

A solution containing 75.61 g (0.60 mol) of crude 4-ethynyl-2,2-dimethyl-[1,3]dioxolane, 100.65 g (0.43 mol) of 5-bromo-thiophene-2-carboxylic acid ethyl ester (J. Am. Chem. Soc., vol. 111 (1989), 7664–7665), 14.84 g (0.01 mol) of tetrakis-(triphenylphosphine)-palladium(0), 4.89 g (0.03 mol) of copper(I) iodide and 119 ml (0.85 mol) of triethylamine in 700 ml of degassed acetonitrile was stirred under argon for 18 hours. The reaction mixture was concentrated under reduced pressure to a thick slurry, which was filtered through a sintered glass filter with washing of the filter cake with hexanes:EtOAc (20:1) and small amounts of $CH_2Cl_2$. The filtrate was concentrated under reduced pressure and the resulting residue was flash-chromatographed on silica gel, eluting 5–16% EtOAc (ethyl acetate) in hexanes. The yield of 5-(2,2-dimethyl-[1,3]dioxolan-4(S)-yl-ethynyl)-thiophene-2-carboxylic acid ethyl ester (1) was 74.61 g (62%) as an amber oil.

$[\alpha]_{589}$+36.6° (c=0.88, MeOH.

IR (neat) 2986, 2226, 1715, 1451, 1255, 1223, 1096, 1065 $cm^{-1}$.

$^1$H NMR ($CDCl_3$) δ: 1.34 (t, 3H, J=7.0 Hz), 1.42 (s, 3H), 1.53 (s, 1H), 4.03 (dd, 1H, J=6.2, 1.8 Hz), 4.34 (dd, 1H, J=6.4, 1.6 Hz), 4.34 (q, 2H, J=7.1 Hz), 4.95 (dd, 1H, J=6.4, 0 Hz), 7.16 (d, 1H, J=3.9 Hz), 7.63 (d, 1H, J=3.9 Hz).

Anal. calc'd for $C_{14}H_{16}O_4S$: C, 59.98; H, 5.75; S, 11.44. Found: C, 59.96; H, 5.71; S, 11.36.

(b) Preparation of 5-[2-(2,2-Dimethyl-[1,3]-diazolan-4(S)-yl)-ethyl]-thiophene-2-cazboxylic acid ethyl ester (2)

(2)

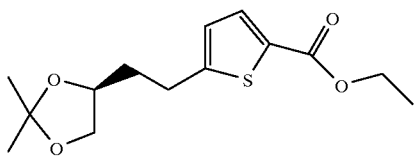

A Parr flask containing 75.10 g (268 mmol) of the acetylene compound (1) and 12.00 g of 5% Pd/C in 500 ml of EtOH (ethanol) was shaken under 45 psi of hydrogen for 3 hours. The mixture was filtered through a pad of Celite (diatomaceous earth material) and the filtrate was concentrated under reduced pressure, yielding 73.25 g (96%) of 5-[2-(2,2-dimethyl-[1,3]-dioxolan-4(S)-yl)-ethyl]-thiophene-2-carboxylic acid ethyl ester (2) as a colorless oil. An analytical sample was obtained by flash chromatography on silica gel, eluting $CH_2Cl_2$.

$[\alpha]_{589}$ −12.1° (c=0.78, MeOH).

IR (neat) 2984, 2938, 2874, 1709, 1462, 1263, 1094, 1069 $cm^{-1}$.

$^1$H NMR ($CDCl_3$) δ: 1.36 (t, 3H, J=7.0 Hz), 1.37 (s, 3H), 1.43 (s, 3H), 1.94 (m, 2H), 2.96 (m, 2H), 3.55 (t, 1H, J=7.3 Hz), 4.04 (dd, 1H, J=6.1, 1.5 Hz), 4.12 (m, 1H), 4.32 (q, 2H, J=7.0 Hz), 6.82 (d, 1H, J=3.7 Hz), 7.63 (d, 1H, J=4.0 Hz)

Anal. calc'd for $C_{14}H_{20}O_4S$: C, 59.13; H, 7.09; S, 11.28. Found: C, 59.23; H, 7.14; S, 11.31.

(c) Preparation of 5-(3(S)-4-Dihydroxy-butyl)-thiophone-2-carboxylic acid ethyl ester (3)

(3)

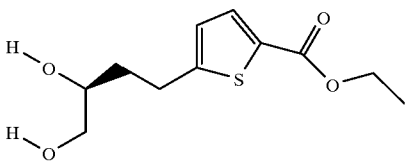

To a stirred solution of 65.98 g (232 mmol) of the acetonide compound (2) in 300 ml of EtOH was added 17.65 g (93 mmol) of p-toluenesulfonic acid monohydrate. The reaction mixture was heated at 65° C. for 3 hours, concentrated under reduced pressure and redissolved in EtOH, and heating was continued. This procedure was repeated until the starting material (2) had disappeared as determined by TLC (thin layer chromatography). The crude reaction was diluted with EtOAc, washed with saturated $NaHCO_3$, washed with saturated NaCl, dried ($MgSO_4$) and concentrated under reduced pressure. The residue was recrystallized from $Et_2O$:hexanes, yielding 49.90 g of the diol (3). The mother liquors were flash-chromatographed on silica gel, eluting 30–100% EtOAc in $CH_2Cl_2$. This yielded another 5.81 g of the diol (3) as a white, low-melting solid. The overall yield of the diol (3) was 55.71 g (98%).

$[\alpha]_{589}$ −28.7° (c=0.82, MeOH).

IR (neat) 3393 (broad), 2936, 1705, 1462, 1287, 1098, 1047 $cm^{-1}$.

$^1$H NMR ($CDCl_3$) δ: 1.36 (t, 3H, J=7.2 Hz), 1.7 (br s, 2H), 1.76 (m, 2H), 2.99 (m, 2H), 3.48 (dd, 1H, J=7.4, 3.5 Hz), 3.68 (dd, 1H, J=7.6, 3.2 Hz), 3.77 (m, 1H), 4.32 (q, 2H, J=7.2 Hz), 6.82 (d, 1H, J=3.9 Hz), 7.63 (d, 1H, J=3.7 Hz)

Anal. calc'd for $C_{11}H_{16}O_4S$: C, 54.08; H, 6.60; S, 13.12. Found: C, 53.81; H, 6.43; S, 13.37.

(d) Preparation of 5-(3(S)-Hydroxy-4-p-tolylmethane-sulfonyloxy-butyl)-thiophene-2-carboxylic acid ethyl ester (4)

(4)

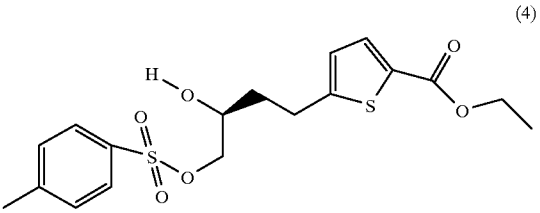

To an ice-cold solution of 45.42 g (186 mmol) of diol (3) and 31.1 ml (223 mmol) of triethylamine in 400 ml of $CH_2Cl_2$ was added 38.99 g (204 mmol) of p-toluenesulfonylchloride. The ice bath was removed and the reaction mixture was stirred at room temperature for 18 hours and poured into 0.5N HCl, and the resulting layers were separated. The aqueous layer was re-extracted with $CH_2Cl_2$. The combined organic layers were washed with saturated NaCl, dried ($MgSO_4$), and concentrated under reduced pressure. The residue was purified by flash chromatography on silica gel, first with 4–100% EtOAc in $CH_2Cl_2$ until the product (4) eluted and then with 0–10% MeOH in EtOAc to elute the starting diol (3). This produced 7.43 g of diol (3) and 49.23 g (66%) of the monotosylate (4) as a lightly colored oil, which solidified on standing.

$[\alpha]_{589}$ −8.2° (c=0.74, MeOH).

IR (neat) 3507 (broad), 2947, 1705, 1462, 1362, 1287, 1177, 1098 $cm^{-1}$.

$^1$H NMR ($CDCl_3$) δ: 1.36 (t, 3H, J=6.9 Hz), 1.78 (m, 2H), 2.46 (s, 3H), 2.95 (m, 2H), 3.90 (m, 2H), 4.03 (m, 1H), 4.32 (q, 2H, J=7.0 Hz), 6.78 (d, 1H, J=3.7 Hz), 7.36 (d, 2H, J=8.2 Hz), 7.61 (d, 1H, J=3.7 Hz), 7.79 (d, 2H, J=8.2 Hz).

Anal. calc'd for $C_{18}H_{22}O_6S_2$: C, 54.25; H, 5.57; S, 16.09. Found: C, 54.13; H, 5.57; S, 16.17.

(e) Preparation of 5-(4-Azido-3(S)-hydroxy-butyl)-thiophene-2-carboxylic acid ethyl ester (5)

(5)

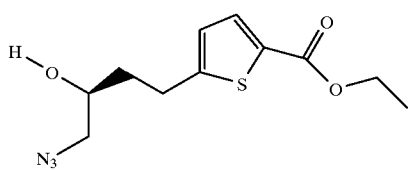

To a stirred solution of 42.94 g (108 mmol) of the tosylate (4) in 250 ml of DMF (N,N-dimethylformamide) was added 31.52 g (485 mmol) of sodium azide. The solution was heated under argon for 4 hours at 80° C. The reaction mixture was cooled and poured into 600 ml of saturated NaCl, and the resulting oil was separated. The aqueous solution was extracted three times with $Et_2O$. The $Et_2O$ extracts were combined with the oil and washed once with saturated NaCl, dried ($MgSO_4$), and concentrated, yielding 33.0 g of the azide (5) as a crude product that was sufficiently pure to use in the next step (f). An analytical sample of the azide (5) was obtained by flash chromatography on silica gel, eluting $CH_2Cl_2$-EtOAc (20:1) to produce a colorless oil.

$[\alpha]_{589}$ −18.8° (c=0.84, MeOH).

IR (neat) 3445 (broad), 2926, 2099, 1705, 1539, 1460, 1281, 1094 $cm^{-1}$.

$^1$H NMR ($CDCl_3$) δ: 1.36 (t, 3H, J=7.1 Hz), 1.85 (m, 2H), 2.99 (m, 2H), 3.35 (m, 2H), 3.79 (m, 1H), 4.32 (q, 2H, J=7.1 Hz), 6.82 (d, 1H, J=3.6 Hz), 7.63 (d, 1H, J=4.0 Hz).

Anal. calc'd for $C_{11}H_{15}N_3O_3S_2$: C, 49.05; H, 5.61; N 15.60; S, 11.90. Found: C, 48.89; H, 5.70; N, 15.37; S, 12.02.

(f) Preparation of 5-(4-tert-Butoxycarbonylamino-3(S)-hydroxy-butyl)-thiophene-2-carboxylic acid ethyl ester (6)

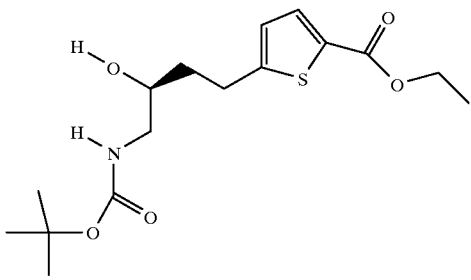

(6)

A Parr flask containing 32.70 g (121 mmol) of the crude azide (5), 27.83 g (127 mmol) of di-tert-butyl dicarbonate, 4.5 g of 5% Pd/C, and 300 ml of THF was shaken under $H_2$ at 30 psi. The exothermic reaction was maintained at a pressure below 45 psi. After 2 hours, the crude mixture was filtered through a pad of Celite and the filtrate was concentrated under reduced pressure. The residue was purified by flash chromatography on silica gel, eluting 6–50% EtOAc in $CH_2Cl_2$. There was thus obtained 35.04 g (84%) of the product (6) as a colorless oil.

$[\alpha]_{589}$ −24.8° (c=0.86, MeOH).

IR (neat) 3391 (broad), 2980, 1723, 1674, 1537, 1462, 1368; 1283, 1171, 1096 cm$^{-1}$.

$^1$H NMR (CDCl$_3$) δ: 1.36 (t, 3H, J=7.0 Hz), 1.45 (s, 9H), 1.81 (m, 2H), 2.94–3.07 (m, 3H), 3.26 (m, 1H), 3.75 (m, 1H), 4.32 (q, 2H, J=7.1 Hz), 4.9 (br s, 1H), 6.82 (d, 1H, J=3.7 Hz), 7.62 (d, 1H, J=4.0 Hz).

Anal. calc'd for $C_{16}H_{25}NO_5S$: C, 55.95; H, 7.34; N, 4.08; S, 9.34. Found: C, 55.89; H, 7.42; N, 4.13; S, 9.45.

(g) Preparation of 5-(4-tert-Butoxycarbonylamino-3(S)-methanesulfonyloxy-butyl)-thiophene-2-carboxylic acid ethyl ester (7)

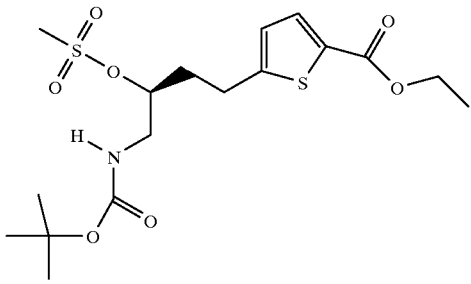

(7)

To an ice-cold solution of 34.34 g (100 mmol) of the alcohol (6) and 20.9 ml (150 mmol) of triethylamine in 250 ml of $CH_2Cl_2$ was added 9.3 ml (120 msol) of methanesulfonyl chloride. After 30 minutes the reaction mixture was poured into 0.5N HCl and the layers were separated. The organic layer was washed with saturated NaHCO$_3$ and then with saturated NaCl, dried (MgSO$_4$), and concentrated under reduced pressure. This produced 38.36 g (91%) of the mesylate (7) as a yellow oil, which solidified on standing. This crude material (7) was used in the next step (h) without further purification.

$^1$H NMR (CDCl$_3$) δ: 1.36 (t, 3H, J=7.0 Hz), 1.44 (s, 9H), 2.09 (m, 2H), 3.00 (m, 2H), 3.08 (s, 3H), 3.34–3.56 (m, 2H), 4.32 (q, 2H, J=7.0 Hz), 4.79 (m, 1H), 4.95 (br t, 1H), 6.82 (d, 1H, J=3.7 Hz), 7.62 (d, 1H, J=3.8 Hz).

(h) Preparation of 5-(3(R)-Acetylsulfanyl-4-tert-butoxycarbonylamino-butyl)-thiophene-2-carboxylic acid ethyl ester (8)

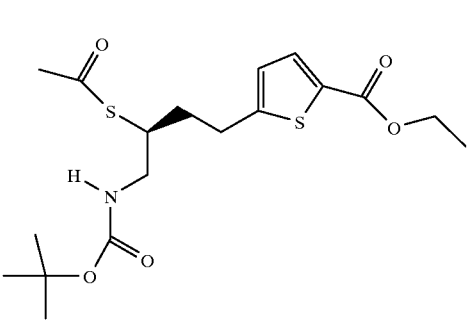

(8)

To a stirred solution of 38.36 g (91.0 mmol) of the crude mesylate (7) in 650 ml of acetone was added 41.57 (364 mmol) of potassium thioacetate. After 14 hours, the starting mesylate (7) had disappeared as determined by TLC and the reaction mixture was a red-brown color and thick with precipitate. The crude reaction mixture was filtered, and the filtered precipitate was washed with acetone and Et$_2$O until it was beige in color. The filtrate was concentrated under reduced pressures to a volume of 500 ml, diluted with EtOAc, washed with saturated NaCl, dried (MgSO$_4$), and concentrated under reduced pressure. The crude oil was purified by flash chromatography on 250 g of-silica gel, eluting hexanes: EtOAc (1:1) to remove baseline-colored impurities. The yield was 39.77 g (109%) of the thioacetate (8) as a red oil, which was used in step (i) without further purification. An analytical sample was obtained by flash chromatography on silica gel, eluting hexanes:EtOAc (4:1), producing a colorless oil.

$[\alpha]_{589}$ +7.6° (c=0.66, MeOH).

IR (neat) 3376, 2978, 2932, 1712, 1684, 1520, 1462, 1263, 1171, 1094 cm$^{-1}$.

$^1$H NMR (CDCl$_3$) δ: 1.35 (t, 3H, J=7.0 Hz), 1.44 (s, 9H), 1.90 (m, 1H), 2.04 (m, 1H), 2.36 (s, 3H), 2.95 (m, 2H), 3.36 (m, 2H), 3.60 (m, 1H), 4.32 (q, 2H, J=7.0 Hz), 4.78 (br t, 1H), 6.78 (d, 1H, J=3.7 Hz), 7.61 (d, 1H, J=3.7 Hz).

Anal. calc'd for $C_{18}H_{27}NO_5S_2$: C, 53.84; H, 6.78; N, 3.49; S, 15.97. Found: C, 53.79; H, 6.87; N, 3.38; S, 15.85.

(i) Preparation of 2-[1-(tert-Butoxycarbonylamino-methyl)-3(R)-(5-ethoxycarbonyl-thiophene-2-yl)-propylsulfanyl]-malonic acid dimethyl ester (9)

(9)

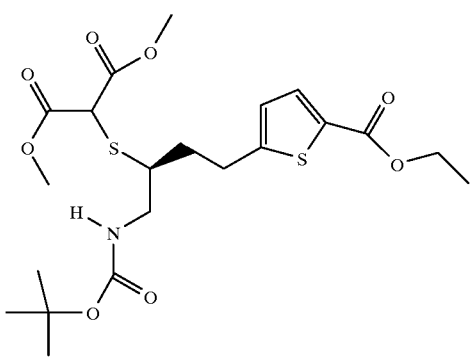

(10)

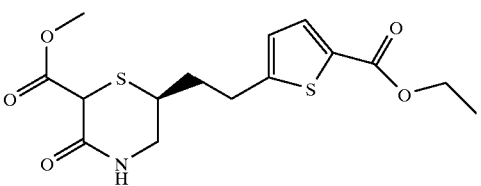

To a stirred, ice-cold solution of 39.77 g (99.0 mmol) of the crude thiolacetate (8) and 13.91 ml (109.0 mmol) of dimethyl chloromalonate in 350 ml of MeOH was added 27.38 g (198.1 mmol) of potassium carbonate. After 3 hours at 0° C. the reaction mixture was stirred at room temperature for 2 hours until the starting (8) material had disappeared (TLC). After pouring into $H_2O$ and extracting with EtOAc (3×), the combined organic layers were washed with saturated NaCl, dried ($MgSO_4$), and concentrated under reduced pressure, producing 49.80 g of a crude disulfide. To a stirred solution of 11.44 g (15.96 mmol) of this disulfide in EtOH under argon was added 1.81 g (47.85 mmol) of sodium borohydride. After 4 hours, the reaction mixture was quenched with 0.5N HCl, diluted with EtOAc, and washed with more 0.5N HCl. The organic layer was washed two times with saturated NaCl, dried ($MgSO_4$), and concentrated under reduced pressure to yield 10.88 g of a crude thiol/disulfide mixture, which was dissolved in degassed MeOH. To this solution was added, while stirring, 5.79 ml (45.36 mmol) of dimethyl chloromalonate and 8.36 g (60.49 mmol) of potassium carbonate. After stirring for 30 minutes under argon, the reaction mixture was diluted with EtOAc, washed twice with saturated NaCl, dried ($MgSO_4$), and concentrated under reduced pressure. The resulting residue was purified by flash chromatography on silica gel, eluting hexanes:EtOAc (3:1). This yielded 4.20 g of the disulfide, which was recycled, and 6.96 g (45%) of the desired malonate (9) as a light-yellow oil.

$[\alpha]_{589}$ +31.9° (c=0.64, MeOH).

IR (neat) 3397, 2978, 2938, 1759, 1715, 1505, 1454, 1275, 1165, 1093, 1020 $cm^{-1}$.

$^1$H NMR (CDCl$_3$) δ: 1.36 (t, 3H, J=7.0 Hz), 1.46 (s, 9H), 1.86 (M, 1H), 2.03 (m, 1H), 3.04 (m, 3H), 3.31 (m, 2H), 3.81 (s, 6H), 4.24 (s, 1H), 4.34 (q, 2H, J=7.0 Hz), 5.13 (br s, 1H), 6.83 (d, 1H, J=3.7 Hz), 7.64 (d, 1H, J=3.7 Hz).

Anal. calc'd for $C_{21}H_{31}NO_8S_2$: C, 51.51; H, 6.38; N, 2.86; S, 13.10. Found: C, 51.29; H, 6.45; N, 2.78; S, 13.01.

(j) Preparation of 6-[2-(5-Ethoxycarbonyl-thiophen-2-yl)-ethyl]-3(R)-oxo-thiomorpholine-2-carboxylic acid methyl ester (10)

To an ice-cold solution of 29.18 g (59.60 mmol) of the malonate (9) in 225 ml of $CH_2Cl_2$ was added 35 ml of trifluoroacetic acid. After 1 hour at 0° C. the reaction mixture showed no starting material by TLC. The reaction mixture was diluted with $CH_2Cl_2$ and continuously washed with saturated $NaHCO_3$, making sure that the aqueous layer was alkaline. The organic layer was washed with saturated NaCl, dried ($MgSO_4$), and concentrated under reduced pressure. The resulting crude amine was dissolved in MeOH and stirred for 2 hours at room temperature. The volatiles were removed under reduced pressure. The resulting crude lactam was flash-chromatographed on silica gel, eluting $CH_2Cl_2$:EtOAc (2:1). This produced 17.74 g (83%) of the desired product (10) as an amber oil.

$[\alpha]_{589}$ +30.9° (c=0.92, MeOH).

IR (neat) 3314, 3242, 2951, 1732, 1660, 1462, 1294, 1157, 1096, 1009 $cm^{-1}$.

$^1$H NMR (CDCl$_3$) δ: 1.36 (t, 3H, J=7.0 Hz), 1.94 (m, 2H), 2.95–3.25 (m, 2H), 3.42–3.67 (m, 3H), 3.79 and 3.82 (s, s, 3H), 4.14 and 4.25 (s, s, 1H), 4.32 (q, 2H, J=7.0 Hz), 6.23 (m, 1H), 6.82 (d, 1H, J=3.7 Hz), 7.63 (d, 1H, J=3.7 Hz).

Anal. calc'd for $C_{15}H_{4}NO_5S_2$: C, 50.40; H, 5.36; N, 3.92; S, 17.94. Found: C, 50.33; H, 5.38; N, 3.82; S, 17.90.

(k) Preparation of 6-[2-(5-Ethoxycarbonyl-thiophen-2-yl)-ethyl]-3(R)-methoxy-5,6-dihydro-2H-[1,4]thiazine-2-carboxylic acid methyl ester (11)

(11)

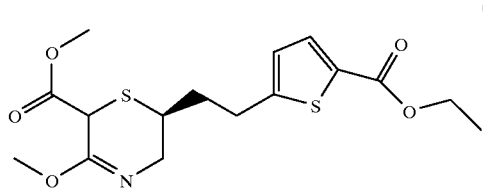

To a stirred solution of 11.799 g (33.01 mmol) of the lactam (10) in 70 ml of $CH_2Cl_2$ was added 6.835 g (46.21 mmol) of trimethyloxonium tetrafluoroborate. After stirring for 18 hours under argon at room temperature all the starting lactam was consumed. The reaction mixture was then cooled, and 50% aqueous $K_2CO_3$ was added until the pH was alkaline. The $KBF_4$ was filtered off and the layers were separated. -The aqueous layer was re-extracted with $CH_2Cl_2$. The combined organic layers were washed with saturated NaCl, dried ($Na_2SO_4$), and concentrated under reduced pressure, yielding 11.55 g (94%) of the crude lactim ether (11), which was used in the next step without further purification.

(l) Preparation of 5-[2-(2-Amino-4-oxo-4,6,7,8-tetrahydro-3H-pyrimido[5,4-b]thiazin-6(R)-yl)-ethyl]-thiophene-2-carboxylic acid ethyl ester (12)

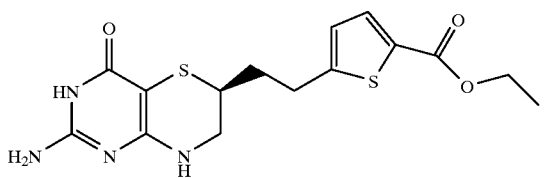

(12)

A solution of sodium ethoxide was prepared by dissolving 0.845 g (36.75 mmol) of sodium metal in degassed absolute ethanol under argon. To this solution was added 3.63 g (38.00 mmol) of guanidine hydrochloride. After stirring for 15 minutes, a solution of 4.55 g (12.25 mmol) of the lactim ether (11) in degassed absolute EtOH was added, and the mixture was heated at reflux for 1 hour. The cooled reaction was neutralized with 0.5N HCl, diluted with EtOAc, and extracted repeatedly. The combined EtOAc layers were washed with saturated NaCl, dried (MgSO$_4$), and concentrated under reduced pressure. The solid residue was slurried in hot EtOH, cooled, and filtered, producing 1.75 g (33%) of the desired product (12) as a light-yellow solid (m.p. 166° C., foams).

$[\alpha]_{589}$ +57.7° (c=0.62, DMSO).

IR (KBr) 3349 (broad), 2926, 1701, 1640, 1603, 1537, 1458, 1344, 1285, 1096 cm$^{-1}$.

$^1$H NMR (DMSO-d$_6$) δ: 1.23 (t, 3H, J=7.0 Hz), 1.80 (m, 2H), 2.82–3.00 (m, 2H), 3.15–3.52 (m, 3H), 4.21 (q, 2H, J=7.0 Hz), 6.00 (s, 2H), 6.64 (s, 1H), 6.95 (d, 1H, J=3.7 Hz), 7.59 (d, 1H, J=3.7 Hz), 10.04 (s, 1H).

HRMS calc'd for C$_{15}$H$_{18}$N$_4$O$_3$S$_2$: (M+Na$^+$) 389.0718. Found: 389.0731.

(m) Preparation of 5-[2-(2-Amino-4-oxo-4,6,7,8-tetrahydro-3H-pyrimido[5,4-b][1,4]thiazin-6(R)-yl)-ethyl]-thiophene-2-carboxylic acid (13)

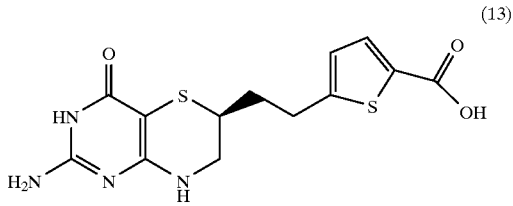

(13)

A solution of 1.152 g (3.14 mmol) of the ester (12) in 10 ml of 1N NaOH was stirred at room temperature for 2 hours. The reaction mixture was filtered to remove some yellowish material. The filtrate was acidified with concentrated HCl and then with 2N HCl to a pH of 3, and the resulting precipitate was collected, washed with a small amount of H$_2$O, and dried. There was thus obtained 894 mg (84%) of the desired acid (13) as an off-white solid (m.p. 283–285° C., with decomp.).

$[\alpha]_{589}$ +71.0° (c=0.60, 1N NaOH).

IR (KBr) 3256 (broad), 2942, 1707, 1641, 1612, 1464, 1364, 1105 cm$^{-1}$.

$^1$H NMR (DMSO-d$_6$) δ: 1.72 (m, 1H), 1.89 (m, 1H), 2.81–3.04 (m, 2H), 3.16–3.52 (m, 3H—partially obscured by H$_2$O), 6.08 (s, 2H), 6.68 (s, 1H), 6.92 (d, 1H, J=4.0 Hz), 7.52 (d, 1H, J=3.7 Hz), 10.12 (s, 1H), 12.80 (br s, 1H).

Anal. calc'd for C$_{13}$H$_{14}$N$_4$O$_3$S$_2$.0.60 H$_2$O: C, 44.71; H, 4.39; N, 16.04; S, 18.36. Found: C, 44.67; H, 4.37; N, 16.00; S, 18.25.

(n) Preparation of 2-{5-[2-(2-Amino-4-oxo-4,6,7,8-tetrahydro-3H-pyrimido[5,4-b][1,4]thiazin-6(R)-yl)-ethyl]-thiophene}-2-L-glutamic acid diethyl ester (14)

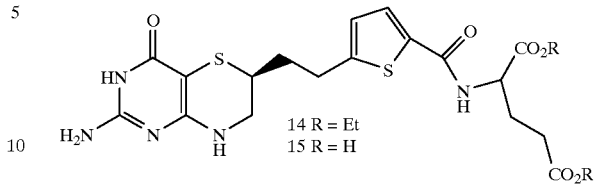

14 R = Et
15 R = H

To a stirred solution of 278 mg (0.82 mmol) of the acid (13), 117 mg (0.87 mmol) of 1-hydroxybenzotriazole, 150 ml (0.87 mmol) of N,N-diisopropylethylamine and 207 mg (0.87 mmol) of L-glutamic acid diethyl ester hydrochloride in 8 ml of DMF, was added 165 mg (0.87 mmol) of 1-(3-dimethylaminopropyl)-3-ethylcarbodiimide hydrochloride. The reaction mixture was stirred under argon for 18 hours and then poured into an ice-cold saturated NaCl solution. The gummy precipitate was collected and the aqueous filtrate was extracted twice with CH$_2$Cl$_2$. The combined precipitate and CH$_2$Cl$_2$ extracts were washed twice with saturated NaCl and then dried (MgSO$_4$). The solvent was removed under reduced pressure and the resulting residue was purified by flash chromatography on silica gel, eluting CH$_2$Cl$_2$:MeOH (10:1). This yielded 282 mg (65%) of the desired glutamate (14) as a white solid (m.p. 108–112° C.).

$[\alpha]_{589}$ +35.0° (c=0.68, DMSO).

IR (KBr) 3343 (broad), 2930, 1732, 1634, 1545, 1450, 1344, 1207, 1024 cm$^{-1}$.

$^1$H NMR (DMSO-d$_6$) δ: 1.13 (t, 3H, J=7.0 Hz), 1.14 (t, 3H, J=7.0 Hz), 1.91 (m, 4H), 2.37 (t, 2H, J=7.3 Hz), 2.89 (m, 2H), 3.23 (m, 2H), 3.49 (m, 1H), 4.00 (q, 2H, J=7.0 Hz), 4.06 (q, 2H, J=7.0 Hz), 4.34 (m, 1H), 6.01 (s, 2H), 6.63 (s, 1H), 6.90 (d, 1H, J=3.7 Hz), 7.66 (d, 1H, J=3.7 Hz), 8.60 (d, 1H, J=7.3 Hz), 10.07 (s, 1H).

Anal. calc'd for C$_{22}$H$_{29}$N$_5$O$_6$S$_2$.1.0 H$_2$O: C, 48.78; H, 5.77; N, 12.93; S, 11.84. Found: C, 48.77; H, 5.72; N, 12.81; S, 11.73.

(o) Preparation of 2-(5-[2-(2-Amino-4-oxo-4,6,7,8-tetrahydro-3H-pyrimido[5,4-b][1,4]thiazin-6(R)-yl)-ethyl]-thiophene)-2-L-glutamic acid (15)

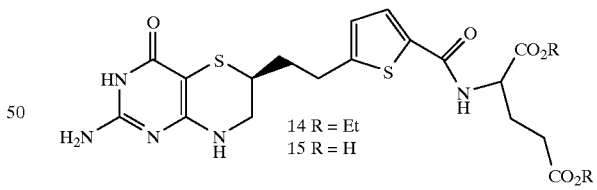

14 R = Et
15 R = H

A solution of 5.068 g (9.68 mmol) of the glutamate (14) in 35 ml of 1N NaOH was stirred at room temperature for 3.5 hours. The reaction mixture was made acidic with concentrated HCl and then with 2N HCl until a pH of about 3. The resulting precipitate was collected by filtration, washed with H$_2$O, and dried in vacuo, yielding 4.486 g (99%) of the desired acid (15) as an off-white solid (m.p. 191–194° C., foams).

$[\alpha]_{589}$ +61.9° (c=0.65, 1N NaOH).

IR (KBr) 3389, 3235, 3086, 2924, 1701, 1624, 1545, 1340, 1148 cmc$^{-1}$.

$^1$H NMR (DMSO-d$_6$) δ: 1.70–2.04 (m, 4H), 2.29 (t, 2H, J=7.3 Hz), 2.90 (m, 2H), 3.13–3.53 (m, 3H—partially obscured by H₂O), 4.29 (m, 1H), 6.30 (s, 2H), 6.77 (s, 1H), 6.89 (d, 1H, J=3.7 Hz), 7.66 (d, 1H, J=3.7 Hz), 8.50 (d, 1H, J=8.1 Hz), 10.30 (br s, 1H).

Anal. calc'd for $C_{18}H_{21}N_5O_6S_2 \cdot 1.80\ H_2O$: C, 43.24; H, 4.96; N, 14.01; S, 12.83. Found: C, 42.88; H, 4.61; N, 13.75; S, 12.60.

Biological and Biochemical Evaluation of Compound (15)

The GAR-transformylase (GARFT) assay method of Young et al., *Biochemistry*, vol. 23 (1984), 3979–3986, was modified and used as described below. Reactions mixtures were prepared containing the catalytic domain of the human GARFT, 0–250 nM test compound, 20 μM glycinamide ribonucleotide (GAR), 10 or 20 μM $N^{10}$-formyl-5,8-dideazafolate (FDDF), 50 mM HEPES-KOH (pH 7.5), and 50 mM KCl. The reaction was initiated with the addition of enzyme to a final concentration of 11 nM, followed by monitoring of the increase in absorbance at 294 nm at 20° C. ($\epsilon_{294}$=18.9 mM$^{-1}$ cm$^{-1}$).

The GARFT inhibition constant ($K_i$) was determined from the dependence of the steady-state catalytic rate on the inhibitor and substrate concentration. The type of inhibition observed was determined to be competitive with respect to FDDF by the dependence of the apparent $K_i$ ($K_{i,app}$) on the concentration of FDDF and was shown to be described by $K_{i,app}=K_i+(K_i/K_m)[\text{FDDF}]$. The Michaelis constant for FDDF, $K_m$, was determined independently by the dependence of the catalytic rate on the FDDF concentration. Data for both the $K_m$ and $K_i$ determinations were fitted by non-linear methods to the Michaelis equation or to the Michaelis equation for competitive inhibition, as appropriate. Data resulting from tight-binding inhibition was analyzed, and $K_i$ was determined by fitting the data to the tight-binding equation of Morrison, *Biochem. Biophys. Acta*, vol. 185 (1969), 269–286, by non-linear methods. Compound (15) was determined to have a GARFT $K_i$ of 3 nM.

EXAMPLE 2

Preparation of 5-(4-tert-Butoxycarbonylamino-3(R)-hydroxy-butyl)-thiophene-2-carboxylic acid ethyl ester (21)

(a) Preparation of 5-[4-(tert-Butyl-dimethyl-silanyloxy)-3(S)-hydroxy-butyl]-thiophene-2-carboxylic acid ethyl ester (16)

(16)

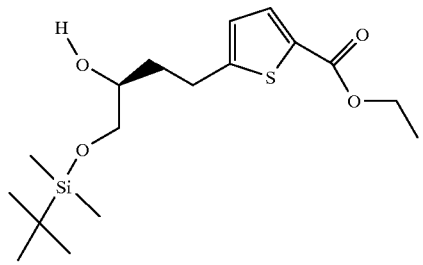

To a stirred, ice-cold solution of 0.946 g (3.87 mmol) of the diol (3) and 0.81 ml (5.81 mmol) of triethylamine in 10 ml of CH₂Cl₂ was added 0.701 g (4.65 mmol) of tert-butyldimethylsilyl chloride. The ice bath was removed and the reaction was stirred at room temperature. After stirring for 24 hours, an additional 117 mg (0.78 mmol) of tert-butyldimethylsilyl chloride and 0.16 ml (1.16 mmol) of triethylamine was added. After stirring for 5 days at room temperature, the reaction mixture was diluted with more CH₂Cl₂ and then washed sequentially with 0.5N HCl, saturated NaHCO₃ and saturated NaCl. The organic layer was dried (MgSO₄) and the solvent was removed under reduced pressure. The resulting crude residue was purified by flash chromatography on silica gel, eluting 0–20% EtOAc in CH₂Cl₂. There was thus obtained 1.252 g (90%) of the desired product (16) as a colorless oil.

[α]₅₈₉ −26.6° (c=0.82, MeOH).

IR (neat) 3486 (broad), 2953, 2930, 2859, 1709, 1462, 1259, 1096 cm⁻¹.

¹H NMR (CDCl₃) δ: 0.07 (s, 6H), 0.90 (s, 9H), 1.36 (t, 3H, J=7.2 Hz), 1.78 (m, 2H), 2.96 (m, 2H), 3.43 (m, 1H), 3.64 (m, 2H), 4.32 (q, 2H, J=7.0 Hz), 6.82 (d, 1H, J=3.7 Hz), 7.62 (d, 1H, J=4.0 Hz).

Anal. calc'd for $C_{17}H_{30}O_4SSi$: C, 56.94; H, 8.43; S, 8.94. Found: C, 56.74; H, 8.43; S, 8.89.

(b) Preparation of 5-[4-(tert-Butyl-dimethyl-silanyloxy)-3(S)-methanesulfonyloxy-butyl]-thiophene-2-carboxylic acid ethyl ester (17)

(17)

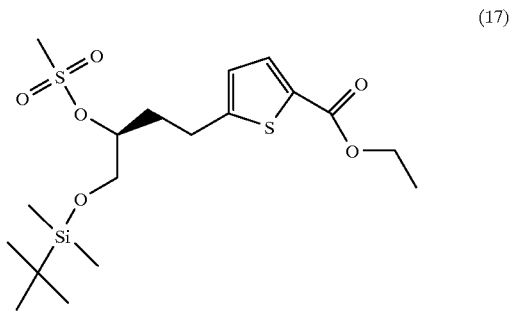

To a stirred, ice-cold solution of 23.19 g (64.68 mmol) of the alcohol (16) and 13.5 ml (96.86 mmol) of triethylamine in 200 ml of CH₂Cl₂ was added 6.0 ml (77.52 mmol) of methanesulfonyl chloride. After 30 minutes at 0° C., the reaction mixture was warmed to room temperature. After another 30 minutes, the reaction mixture was diluted with CH₂Cl₂ and then washed sequentially with 0.5N HCl, saturated NaHCO₃ and saturated NaCl. The organic layer was dried (MgSO₄) and the solvent was removed under reduced pressure, yielding 26.61 g (94%) of the desired mesylate (17) as a colorless oil, which was used in the next step without further purification.

¹H NMR (CDCl₃) δ: 0.11 (s, 3H), 0.13 (s, 3H), 0.92 (s, 9H), 1.39 (t, 3H, J=7.0 Hz), 2.08 (m, 2H), 3.03 (m, 2H), 3.10 (s, 3H), 3.80 (m, 2H), 4.36 (q, 2H, J=7.0 Hz), 4.75 (m, 1H), 6.88 (d, 1H, J=3.7 Hz), 7.66 (d 1H, J=3.7 Hz).

(c) Preparation of 5-(4-Hydroxy-3(S)-methane-sulfonyloxy-butyl)-thiophene-2-carboxylic acid ethyl ester (18)

(18)

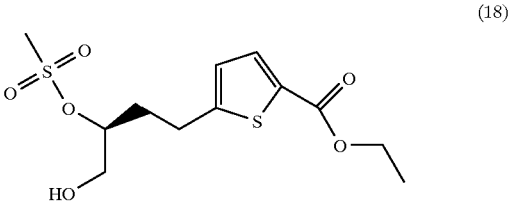

To a stirred solution of 26.56 g (60.83 mmol) of protected alcohol (17) in 200 ml of THF (tetrahydrofuran) was added 67 ml (67.00 mmol) of a 1.0 M solution of tetrabutylammonium fluoride in THF. After stirring for 1.5 hours at room temperature, the reaction mixture was diluted with EtOAc and washed with 0.5N HCl. The aqueous layer was re-extracted with EtOAc. The combined organic layers were washed twice with saturated NaCl, dried (MgSO$_4$), and concentrated under reduced pressure. The residue was flash-chromatographed on silica gel, eluting 0–20% EtOAc in CH$_2$Cl$_2$. This yielded 12.465 g (64%) of the desired product (18) as a colorless oil, which solidified on standing.

[α]$_{589}$ −4.3° (c=0.78, MeOH).

IR (neat) 3520, 2982, 2940, 1705, 1684, 1462, 1345, 1287, 1173, 1098 cm$^{-1}$.

$^1$H NMR (CDCl$_3$) δ: 1.36 (t, 3H, J=7.0 Hz), 2.09 (m, 2H), 3.01 (m, 2H), 3.12 (s, 3H), 3.80 (m, 2H), 4.32 (q, 2H, J=7.0 Hz), 4.81 (m, 1H), 6.86 (d, 1H, J=3.7 Hz), 7.63 (d, 1H, J=3.7 Hz).

Anal. calc'd for C$_{12}$H$_{18}$O$_6$S$_2$: C, 44.70; H, 5.63; S, 19.89. Found: C, 44.75; H, 5.70; S, 19.82.

(d) Preparation of 5-(2(R)-Oxiranyl-ethyl)-thiophene-2-carboxylic acid ethyl ester (19)

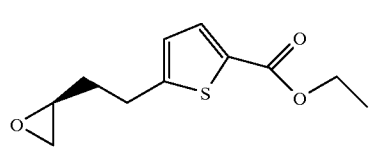

(19)

To a stirred, ice-cold solution of 559 mg (1.73 mmol) of the mesylate (18) in 10 ml of THF was added 76 mg (1.90 mmol) of a 60% dispersion of sodium hydride (NaH) in mineral oil. After 1 hour, the ice bath was removed and the reaction was stirred at room temperature. After stirring for 18 hours, another 35 mg (0.88 mmol) of a 60% dispersion of NaH was added. After 4 days of stirring, the reaction mixture was diluted with EtOAc, washed with 0.5N HCl and then with saturated NaCl, dried (MgSO$_4$), and concentrated under reduced pressure. The resulting crude residue was flash-chromatographed on silica gel, eluting CH$_2$Cl$_2$. Consequently, 322 mg (82%) of the desired epoxide (19) was obtained as a colorless oil.

[α]$_{589}$ +19.6° (c=1.14, MeOH).

IR (neat) 2984, 1707, 1460, 1283 1262, 1092 cm$^{-1}$.

$^1$H NMR (CDCl$_3$) δ: 1.36 (t, 3H, J=7.0 Hz), 1.80–2.05 (m, 2H), 2.51 (dd, 1H, J=4.8, 2.6 Hz), 2.78 (dd, 1H, J=4.8, 4.1 Hz), 2.99 (m, 3H), 4.32 (q, 2H, J=7.0 Hz), 6.82 (d, 1H, J=3.7 Hz), 7.63 (d, 1H, J=3.7 Hz).

Anal. calc'd for C$_{11}$H$_{14}$O$_3$S: C, 58.38; H, 6.24; S, 14.17. Found: C, 58.49; H, 6.29; S, 14.06.

(e) Preparation of 5-(4-Azido-3(R)-hydroxy-butyl)-thiophene-2-carboxylic acid ethyl ester (20)

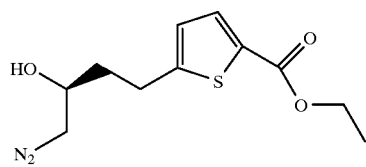

(20)

To a stirred solution of 200 mg (0.88 mmol) of the epoxide (19) in 10 ml of CH$_3$CN was added 296 mg (1.33 mmol) of magnesium perchlorate. After 10 minutes, the reaction mixture became homogeneous and 144 mg (2.21 mmol) of sodium azide was added. The reaction mixture was heated to 75° C. After 18 hours, 25 mg (0.39 mmol) of sodium azide was added and heating was continued for another 18 hours. The reaction mixture was cooled and diluted with EtOAc, and was then washed with saturated NaCl. The aqueous layer was re-extracted with EtOAc. The combined organic layers were washed with saturated NaCl, dried (MgSO$_4$), and concentrated under reduced pressure. The residue was flash-chromatographed on silica gel, eluting 20–25% EtOAc in hexanes. This produced 187 mg (79%) of the azide (20) as a colorless oil.

[α]$_{589}$ +18.9° (c=0.62, MeOH).

IR (neat) 3462 (broad), 2982, 2936, 2101, 1705, 1682, 1462, 1269, 1096 cm$^{-1}$.

$^1$H NMR (CDCl$_3$) δ: 1.36 (t, 3H, J=7.0 Hz), 1.85 (m, 2H), 2.99 (m, 2H), 3.30 (m, 2H), 3.79 (m, 1H), 4.32 (q, 2H, J=7.0 Hz), 6.82 (d, 1H, J=3.7 Hz), 7.63 (d, 1H, J=3.7 Hz).

Anal. calc'd for C$_{11}$H$_{15}$O$_3$S: C, 49.05; H, 5.61; N, 15.60; S, 11.90. Found: C, 48.97; H, 5.64; N, 15.51; S, 11.97.

(f) Preparation of 5-(4-tert-Butoxycarbonylamino-3(R)-hydroxybutyl)-thiophene-2-carboxylic acid ethyl ester (21)

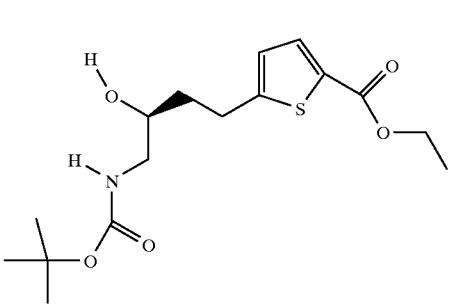

(21)

A solution of 144 mg (0.53 mmol) of the azide (20), 14 mg of 5% Pd/C and 128 mg (0.59 mmol) of di-tert-butyl dicarbonate in 10 ml of THF was stirred vigorously under 1 atmosphere of H$_2$ for 18 hours. The reaction mixture was filtered through Celite and the solvent was removed under reduced pressure. The residue was flash-chromatographed on silica gel, eluting 9–20% EtOAc in CH$_2$Cl$_2$. This yielded 166 mg (90%) of the desired product (21) as a colorless oil.

[α]$_{589}$ +26.3° (c=0.76, MeOH).

IR (neat) 3378 (broad), 2980, 2934, 1715, 1682, 1516, 1462, 1294, 1099 cm$^{-1}$.

$^1$H NMR (CDCl$_3$) δ: 1.33 (t, 3H, J=7.0 Hz), 1.44 (s, 9H), 1.79 (m, 2H), 2.22 (br s, 1H), 3.04 (m, 3H), 3.25 (m, 1H), 3.73 (m, 1H), 4.32 (q, 2H, J=7.0 Hz), 6.81 (d, 1H, J=3.7 Hz), 7.62 (d, 1H, J=3.7 Hz).

Anal. calc'd for C$_{16}$H$_{25}$NO$_5$S: C, 55.95; H, 7.34; N, 4.08; S, 9.34. Found: C, 55.88; H, 7.35; N, 4.01; S, 9.40.

(g) Preparation of 5-(4-tert-Butoxycarbonylamino-3(R)-methanesulfonyloxy-butyl)-thiophene-2-carboxylic acid ethyl ester (22)

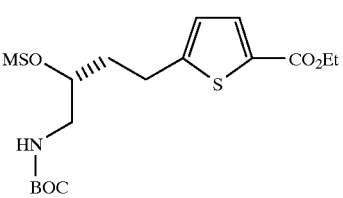

22

Starting with alcohol (21), compound (22) was prepared in 94% crude yield according to the general procedure described for compound (7).

$^1$H NMR (CDCl$_3$) δ: 1.36 (t, 3H, J=7.0 Hz), 1.45 (s, 9H), 2.07 (m, 2H), 3.00 (m, 2H), 3.06 (s, 3H), 3.37–3.50 (m, 2H), 4.32 (q, 2H, J=7.0 Hz), 4.78 (m, 1H), 4.91 (br t, 1H), 6.84 (d, 1H, J=4.0 Hz), 7.62 (d, 1H, J=4.0 Hz).

(h) Preparation of 5-(3(S)-Acetylsulfanyl-4-tert-butoxycarbonylamino-butyl)-thiophene-2-carboxylic acid ethyl ester (23)

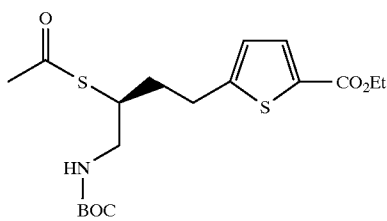

23

Starting with mesylate (22), compound (23) was prepared in 86% yield according to the general procedure described for compound (8).

$[\alpha]_{589}$ −4.9° (c=0.61, MeOH).

IR (neat) 3374, 2978, 2932, 1715, 1695, 1518, 1460, 1264, 1171, 1096 cm$^{-1}$.

$^1$H NMR (CDCl$_3$) δ: 1.35 (t, 3H, J=7.0 Hz), 1.44 (s, 9H), 1.90 (m, 1H), 2.03 (m, 1H), 2.36 (s, 3H), 2.95 (m, 2H), 3.35 (m, 2H), 3.59 (m, 1H), 4.31 (2H, q, J=7.0 Hz), 4.74 (br t, 1H), 6.79 (d, 1H, J=3.7 Hz), 7.62 (d, 1H, J=3.7 Hz).

Anal. calc'd for C$_{18}$H$_{27}$NO$_5$S$_2$: C, 53.84; H, 6.78; N, 3.49; S, 15.97. Found: C, 53.75; H, 6.86; N, 3.43; S, 16.07.

(i) Preparation of 2-[1-(tert-Butoxycarbonylamino-methyl)-3(S)-(5-ethoxycarbonyl-thiophen-2-yl)-propylsulfanyl]-malonic acid dimethyl ester (24)

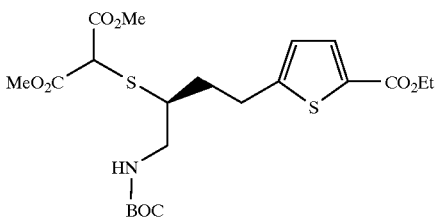

24

To a stirred solution of 8.44 g (21.0 mmol) of thioacetate (23) and 3.22 ml (25.2 mmol) of dimethyl chloromalonate in 75 ml of degassed methanol at 0° C. was added 5.81 g (42.0 mmol) of potassium carbonate. The reaction, under an Ar atmosphere, was allowed to stir for 1 hr at 0° C., then 1.5 hr at rt, poured into saturated NaCl and extracted twice with EtOAc. The combined organic layer was washed twice more with saturated NaCl solution, dried (MgSO$_4$), and concentrated under reduced pressure. The resulting residue was purified by flash chromatography on silica gel, eluting hexanes:EtOAc (3:1). This produced 9.678 g (94%) of the desired malonate (24) as a yellow oil.

$[\alpha]_{589}$ −32.8° (c=0.67, MeOH).

IR (neat) 3395 (broad), 2978, 1755, 1715, 1699, 1462, 1261 cm$^{-1}$.

$^1$H NMR (CDCl$_3$) δ: 1.36 (t, 3H, J=7.0 Hz), 1.44 (s, 9H), 1.86 (m, 1H), 2.05 (m, 1H), 3.02 (m, 3H), 3.31 (m, 2H), 3.79 (s, 6H), 4.23 (s, 1H), 4.33 (q, 2H, J=7.0 Hz), 6.81 (d, 1H, J=3.7 Hz), 7.62 (d, 1H, J=3.7 Hz).

Anal. Calc'd for C$_{21}$H$_{30}$NO$_8$S$_2$: C, 51.51; H, 6.38; N, 2.86; S, 13.10. Found: C, 51.58; H, 6.42; N, 2.79; S, 13.01.

(j) Preparation of 6-[2-(5-Buthoxycarbonyl-thiophen-2-yl)-ethyl]-3(S)-oxo-thiomorpholine-2-carboxylic acid ethyl ester (25)

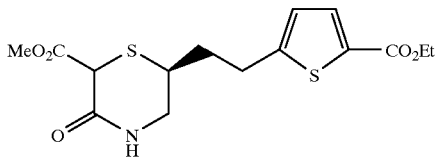

25

Starting with malonate (24), compound (25) was prepared in 86% yield according to the general procedure described for compound (10).

$[\alpha]_{589}$ −30.5° (c=1.01, MeOH).

IR (neat) 3320, 3229, 2951, 1738, 1703, 1669, 1460, 1281 cm$^{-1}$.

$^1$H NMR (CDCl$_3$) δ: 1.36 (t, 3H, J=7.0 Hz), 1.91–2.04 (m, 2H), 2.95–3.25 (m, 2H), 3.42–3.65 (m, 3H), 3.79 and 3.82 (s, s, 3H), 4.13 and 4.25 (s, s, 1H), 4.32 (q, 2H, J=7.0 Hz), 6.26 (m, 1H), 6.82 (d, 1H, J=3.7 Hz), 7.64 (d, 1H, J=3.7 Hz).

Anal. calc'd for C$_{15}$H$_{19}$NO$_5$S$_2$: C, 50.40; H, 5.36; N, 3.92; S, 17.94. Found: C, 50.47; H, 5.34; N, 3.95; S, 17.84.

(k) Preparation of 6-[2-(5-Buthoxycarbonyl-thiophen-2-yl)-ethyl]-3(S)-methoxy-5,6-dihydro-2H-[1,4]thiazine-2-carboxylic acid ethyl ester (26)

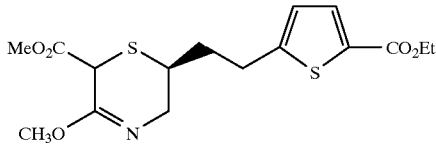

26

Starting with lactam (25), compound (26) was prepared in quantitative crude yield according to the general procedure described for compound (11) and was used in the next step without purification.

(l) Preparation of 5-[2-(2-Amino-4-oxo-4,6,7,8-tetrahydro-3H-pyrimido[5,4-b]thiazin-6(S)-yl)-ethyl]-thiophene-2-carboxylic acid ethyl ester (27)

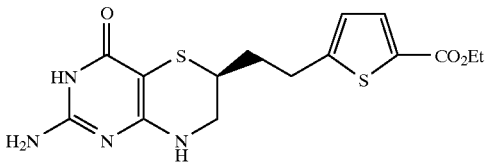

27

Starting with lactim ether (26), compound (27) was prepared in 45% yield according to the general procedure described for compound (12). (m.p. 181–184° C.).

$[\alpha]_{589}$ −59.7° (c=0.38, DMSO).

IR (KBr) 3335, 2926, 1705, 1632, 1593, 1456, 1335, 1260 cm$^{-1}$.

$^1$H NMR (DMSO-d$_6$) δ: 1.23 (t, 3H, J=7.0 Hz), 1.72 (m, 1H), 1.88 (m, 1H), 2.81–3.00 (m, 2H), 3.16–3.52 (m, 3H), 4.22 (q, 2H, J=7.0 Hz), 6.00 (s, 2H), 6.65 (s, 1H), 6.96 (d, 1H, J=3.7 Hz), 7.60 (d, 1H, J=3.7 Hz), 10.04 (s, 1H).

Anal. calc'd for C$_{15}$H$_{18}$N$_4$O$_3$S$_2$.0.4 H$_2$O.0.5EtOH: C, 48.44; H, 5.54; N, 14.12; S. 16.17. Found: C, 48.69; H. 5.52; N, 14.07; S, 16.00.

(m) Preparation of 5-[2-(2-Amino-4-oxo-4,6,7,8-tetrahydro-3H-pyrimido[5,4-b][1,4]thiazin-6(S)-yl)-ethyl]thiophene-2-carboxylic acid (28)

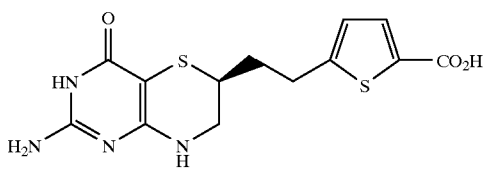

Starting with ester (27), compound (28) was prepared in 98% yield according to the general procedure described for compound (13). (m.p. 258–261° C., with decomp.).

[α]$_{589}$ −81.3° (c=0.63, 1N NaOH).

IR (KBr) 3254 (broad), 2918, 1692, 1635, 1458, 1352, 1101 cm$^{-1}$.

$^1$H NMR (DMSO-d$_6$) δ: 1.72 (m, 1H), 1.89 (m, 1H), 2.80–3.03 (m, 2H), 3.16–3.52 (m, 3H—partially obscured by H$_2$O), 6.09 (s, 2H), 6.80 (s, 1H), 6.92 (d, 1H, J=3.7 Hz), 7.52 (d, 1H, J=3.7 Hz), 10.20 (s, 1H), 12.80 (br s, 1H).

HRMS calc'd for C$_{13}$H$_{14}$N$_4$O$_3$S$_2$: (M+Na+) 361.0405. Found: 361.0390.

(n) Preparation of 2-({5-[2-(2-Amino-4-oxo-4,6,7,8-tetrahydro-3H-pyrimido[5,4-b][1,4]thiazin-6(S)-yl)-ethyl]-thiophene)-2-L-glutamic acid diethyl ester (29)

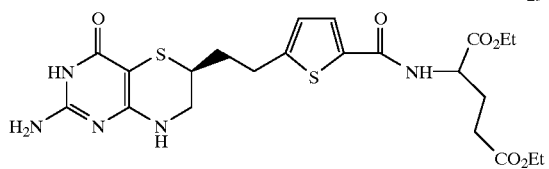

Starting with acid (28), compound (29) was prepared in 60% yield according to the general procedure described for compound (14). (m.p. 105–110° C., with foaming).

[α]$_{589}$ −55.5° (c=0.53, DMSO).

IR (Br) 3345, 2930, 1734, 1653, 1636, 1541, 1456, 1345 cm$^{-1}$.

$^1$H NMR (DMSO-d$_6$) δ: 1.12 (t, 3H, J=7.0 Hz), 1.14 (t, 3H, J=7.0 Hz), 1.75–2.03 (m, 4H), 2.37 (t, 2H, J=7.4 Hz), 2.88 (m, 2H), 3.17 (m, 2H), 3.47 (m, 1H), 4.01 (q, 2H, J=7.0 Hz), 4.07 (q, 2H, J=7.0 Hz), 4.34 (m, 1H), 6.00 (s, 2H), 6.64 (s, 1H), 6.89 (d, 1H, J=3.7 Hz), 7.65 (d, 1H, J=3.7 Hz), 8.60 (d, 1H, J=7.3 Hz), 10.05 (s, 1H).

Anal. calc'd for C$_{22}$H$_{29}$N$_5$O$_6$S$_2$.1.0 H$_2$O: C, 48.78; H, 5.77; N, 12.93; S, 11.84. Found: C, 48.73; H, 5.74; N, 12.96; S, 11.92.

(o) Preparation of 2-(5-[2-(2-Amino-4-oxo-4,6,7,8-tetrahydro-3H-pyrimido[5,4-b][1,4]thiazin-6(S)-yl)-ethyl]-thiophene)-2-L-glutamic acid (30)

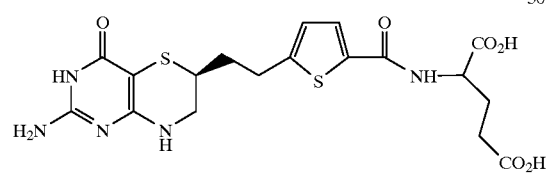

Starting with diester (29), compound (30) was prepared in 97% yield according to the procedure described for compound (15). (m.p. 220° C. with decomposition).

[α]$_{589}$ −57.1° (c=0.61, 1N NaOH)

IR(KBr) 3353, 3094, 2926, 1711, 1641, 1605, 1559, 1454, 1400, 1333, 1279, 1080 cm$^{-1}$.

$^1$H NMR (DMSO-d$_6$) δ: 1.70–2.05 (m, 4H), 2.29 (t, 2H, J=7.4 Hz), 2.87 (m, 2H), 3.15–3.48 (m, 3H—partially obscured by H$_2$O), 4.29 (m, 1H), 6.03 (s, 2H), 6.66 (s, 1H), 6.89 (d, 1H, J=3.7 Hz), 7.65 (d, 1H, J=3.7 Hz), 8.50 (d, 1H, J=7.7 Hz), 10.05 (s, 1H), 12.50 (br s, 2H).

Anal. calc'd for C$_{18}$H$_{21}$N$_5$O$_6$S$_2$.1.4 H$_2$O: C, 43.87; H, 4.87; N, 14.21; S, 13.01. Found: C, 43.83; H, 4.78; N, 14.10; S, 12.90.

EXAMPLE 3

Preparation of 5-{2-[2-(2-Amino-4-oxo-4,6,7,8-tetrahydro-3H-pyrimido[5,4-b][1,4]thiazin-6(R)-yl)-ethyl]-4-methyl-thiophene}-2-L-glutamic acid (45)

(a) Preparation of 5-(2,2-Dimethyl-[1,3]dioxolan-4(S)-yl-ethynyl)-4-methyl-thiophene-2-carboxylic acid ethyl ester (31)

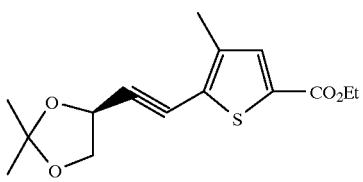

Starting with 4(S)-Ethynyl-2,2-dimethyl-[1,3]dioxolane and 2-Bromo-3-methyl-thiophene-5-carboxylic acid ethyl ester, prepared according to M. Nemec, *Collection Czechoslov. Chem. Commun.*, compound (31) was prepared in 67% yield according to the general procedure described for compound (1).

[α]$_{589}$ +36.7° (c=1.04, MeOH).

IR(neat) 2986, 2936, 2222, 1711, 1441, 1283, 1244, 1190 cm$^{-1}$.

$^1$H NMR (CDCl$_3$) δ: 1.36 (t, 3H, J=7.0 Hz), 1.42 (s, 3H), 1.53 (s, 3H), 2.29 (9, 3H), 4.04 (dd, 1H, J=6.2, 1.8 Hz), 4.26 (dd, 1H, J=6.2, 1.8 Hz), 4.32 (q, 2H, J=7.0 Hz), 4.99 (t, 1H, J=6.0 Hz), 7.50 (9, 1H).

Anal. calc'd for C$_{15}$H$_{18}$O$_4$S: C, 61.20; H, 6.16; S, 10.89. Found: C, 61.33; H, 6.21; S, 10.78.

(b) Preparation of 5-[2-(2,2-Dimethyl-[1,3]-dioxolan-4(S)-yl)-ethyl]-3-methyl-thiophene-2-carboxylic acid ethyl ester (32)

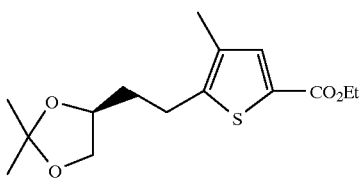

Starting with alkyne (31), compound (32) was prepared in 98% yield according to the general procedure described for compound (2).

[α]$_{589}$ −12.6° (c=0.94, MeOH).

IR (neat) 2984, 2936, 2872, 1707, 1456, 1371, 1246, 1069 cm$^{-1}$.

$^1$H NMR (CDCl$_3$) δ: 1.35 (t, 3H, J=7.0 Hz), 1.36 (s, 3H), 1.43 (s, 3H), 1.88 (m, 2H), 2.16 (s, 3H), 2.80–2.91 (m, 2H), 3.55 (dd, 1H, J=6.6, 0.7 Hz), 4.03 (dd, 1H, J=5.9, 1.8 Hz), 4.12 (m, 1H), 4.31 (q, 2H, J=7.0 Hz), 7.50 (s, 1H).

Anal. calc'd for C$_{15}$H$_{22}$O$_4$S: C, 60.37; H, 7.43; S, 10.75. Found: C, 60.42; H, 7.48; S, 10.68.

(c) Preparation of 5-(3(S)-4-Dihydroxybutyl)-4-methyl-thiophene-2-carboxylic acid ethyl ester (33)

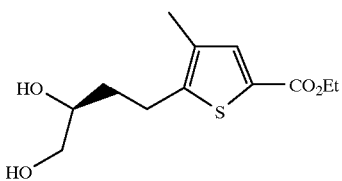

33

Starting with dioxolane (32), compound (33) was prepared in 92% yield according to the general procedure described for compound (3).

$[\alpha]_{589}$ −24.3° (c=0.61, MeOH).

IR (KBr) 3264 (broad), 2924, 1707, 1458, 1447, 1260, 1179, 1074 cm$^{-1}$.

$^1$H NMR (CDCl$_3$) δ: 1.35 (t, 3H, J=7.0 Hz), 1.76 (m, 2H), 2.17 (s, 3H), 2.89 (m, 2H), 3.48 (dd, 1H, J=7.4, 3.3 Hz), 3.68 (dd, 1H, J=7.7, 3.3 Hz), 3.75 (m, 1H), 4.30 (q, 2H, J=7.0 Hz), 7.50 (s, 1H).

Anal. calc'd for C$_{12}$H$_{18}$O$_4$S: C, 55.79; H, 7.02; S, 12.41. Found: C, 55.69; H, 6.99; S, 12.31.

(d) Preparation of 5-(3(S)-Hydroxy-4-p-tolylmethanesulfonyloxy-butyl)-4-methyl-thiophene-2-carboxylic acid ethyl ester (34)

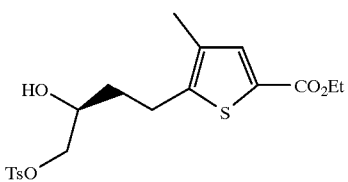

34

Starting with diol (33), compound (34) was prepared in 60% yield according to the general procedure described for compound (4).

$[\alpha]_{589}$ −5.7° (c=0.74, MeOH).

IR (neat) 3491 (broad), 2982, 2928, 1703, 1449, 1360, 1250, 1177 cm$^{-1}$.

$^1$H NMR (CDCl$_3$) δ: 1.35 (t, 3H, J=7.0 Hz), 1.71 (m, 2H), 2.13 (s, 3H), 2.46 (s, 3H), 2.85 (m, 2H), 3.88–4.03 (m, 3H), 4.31 (q, 2H, J=7.0 Hz), 7.36 (d, 2H, J=8.1 Hz), 7.48 (s, 1H), 7.79 (d, 2H, J=8.4 Hz).

Anal. calc'd for C$_{19}$H$_{24}$O$_6$S$_2$: C, 55.32; H, 5.86; S, 15.55. Found: C, 55.37; H, 5.92; S, 15.48.

(e) Preparation of 5-(4-Azido-3(S)-hydroxy-butyl)-4-methyl-thiophene-2-carboxylic acid ethyl ester (35)

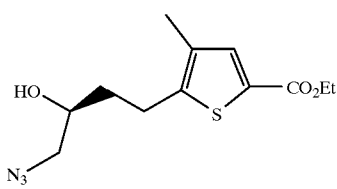

35

Starting with tosylate (34), compound (35) was prepared in 96% crude yield according to the general procedure described for compound (5) and used without purification.

$^1$H NMR (CDCl$_3$) δ: 1.36 (t, 3H, J=7.0 Hz), 1.80 (m, 2H), 2.16 (s, 3H), 2.83–2.96 (m, 2H), 3.29 (dd, 1H, J=12.1, 7.4 Hz), 3.40 (dd, 1H, J=12.1, 3.7 Hz), 3.78 (m, 1H), 4.30 (q, 2H, J=7.0 Hz), 7.50 (s, 1H).

(f) Preparation of 5-(4-tert-Butoxycarbonylamino-3(S)-hydroxy-butyl)-4-methyl-thiophene-2-carboxylic acid ethyl ester (36)

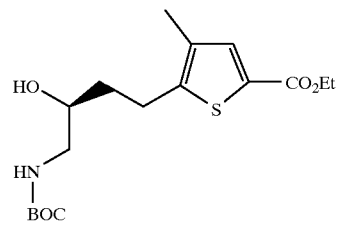

36

Starting with azide (35), compound (36) was prepared in 89% yield according to the general procedure described for compound (6).

$[\alpha]_{589}$ −21.7° (c=0.71, MeOH).

IR (neat) 3385 (broad), 2978, 2932, 1715, 1682, 1520, 1454, 1254, 1177, 1073 cm$^{-1}$.

$^1$H NMR (CDCl$_3$) δ: 1.35 (t, 3H, J=7.0 Hz), 1.44 (s, 9H), 1.75 (m, 2H), 2.16 (s, 3H), 2.80–2.94 (m, 2H), 3.08 (dd, 1H, J=14.3, 7.4 Hz), 3.28 (dd, 1H, J=14.3, 3.0 Hz), 3.74 (m, 1H), 4.30 (q, 2H, J=7.0 Hz), 7.49 (s, 1H).

Anal. calc'd for C$_{17}$H$_{27}$NO$_5$S: C, 57.12; H, 7.61; N, 3.92; S, 8.97. Found: C, 57.05; H, 7.65; N, 3.96; S, 9.07.

(g) Preparation of 5-(4-tert-Butoxycarbonylamino-3(S)-methanesulfonyloxy-butyl)-4-methyl-thiophene-2-carboxylic acid ethyl ester (37)

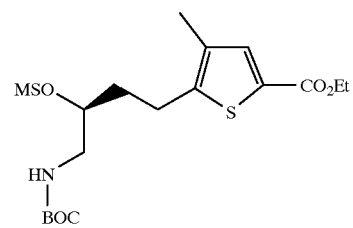

37

Starting with alcohol (36), compound (37) was prepared in 94% yield according to the general procedure described for compound (7) (m.p. 75–76° C.).

$[\alpha]_{589}$ +7.8° (c=0.60, MeOH).

IR (KBr) 3362, 2982, 1699, 1680, 1530, 1350, 1278, 1175, 1071 cm$^{-1}$.

$^1$H NMR (CDCl$_3$) δ: 1.35 (t, 3H, J=7.0 Hz), 1.45 (s, 9H), 2.01 (m, 2H), 2.16 (s, 3H), 2.89 (m, 2H), 3.07 (s, 3H), 3.30–3.48 (m, 2H), 4.31 (q, 2H, J=7.0 Hz), 4.80 (m, 1H), 4.95 (br t, 1H), 7.50 (s, 1H).

Anal. calc'd for C$_{18}$H$_{29}$NO$_7$S$_2$: C, 49.63; H, 6.71; N, 3.22; S, 14.72. Found: C, 49.72; H, 6.76; N. 3.26; S, 14.82.

(h) Preparation of 5-(3(R)-Acetylsulfanyl-4-tert-butoxycarbonylamino-butyl)-4-methyl-thiophene-2-carboxylic acid ethyl ester (38)

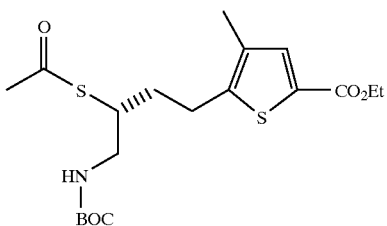

38

Starting with mesylate (37), compound (38) was prepared in 96% yield according to the general procedure described for compound (8).

[α]$_{589}$ −2.8° (c=0.78, MeOH).

IR (neat) 3376, 2978, 2932, 1699, 1516, 1454, 1250, 1173, 1073 cm$^{-1}$.

$^1$H NMR (CDCl$_3$) δ: 1.34 (t, 3H, J=7.0 Hz), 1.44 (s, 9H), 1.80–2.04 (m, 2H), 2.13 (s, 3H), 2.37 (s, 3H), 2.85 (m, 2H), 3.38 (m, 2H), 3.60 (m, 1H), 4.30 (q, 2H, J=7.0 Hz), 4.88 (br t, 1H), 7.48 (s, 1H).

Anal. calc'd for C$_{19}$H$_{29}$NO$_5$S$_2$: C, 54.91; H, 7.03; N, 3.37; S, 15.43. Found: C, 54.97; H, 7.05; N, 3.39; S, 15.32.

(i) Preparation of 2-[1-(tert-Butoxycarbonylamino-methyl)-3(R)-(5-ethoxycarbonyl-3-methyl-thiophene-2-yl)-propylsulfinyl]-malonic acid dimethyl ester (39)

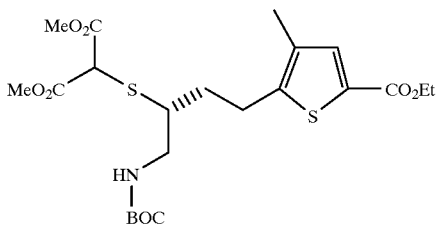

39

Starting with thioacetate (38), compound (39) was prepared in 90% yield according to the general procedure described for compound (24).

[α]$_{589}$ +22.7° (c=0.67, MeOH).

IR (neat) 3397, 2978, 1755, 1714, 1514, 1454, 1250, 1171, 1074 cm$^{-1}$.

$^1$H NMR (CDCl$_3$) δ: 1.34 (t, 3H, J=7.0 Hz), 1.44 (s, 9H), 1.92 (m, 2H), 2.15 (s, 3H), 2.95–3.40 (m, 5H), 3.80 and 3.82 (s, s, 6H), 4.23 (s, 1H), 4.31 (q, 2H, J=7.0 Hz), 5.18 (br s, 1H), 7.49 (s, 1H).

Anal. calc'd for C$_{22}$H$_{33}$NO$_8$S: C, 52.46; H, 6.61; N, 2.78; S, 12.73. Found: C, 52.56; H, 6.62; N, 2.81; S, 12.71.

(j) Preparation of 6-[2-(5-Buthoxycarbonyl-3-methyl-thiopen-2-yl)-ethyl]-3(R)-oxo-thiomorpholine-2-carboxylic acid methyl ester (40)

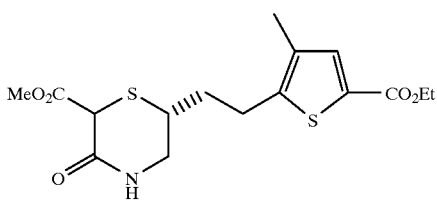

40

Starting with compound (39), compound (40) was prepared in 87% yield according to the general procedure described for compound (10). (m.p. 72–73° C.).

[α] +19.1° (c=0.67, MeOH).

IR (thinfilm) 2954, 1738, 1694, 1651, 1464, 1296, 1196, 1074 cm$^{-1}$.

$^1$H NMR (CDCl$_3$) δ: 1.35 (t, 3H, J=7.0 Hz), 1.90 (m, 2H), 2.17 (s, 3H), 2.88 (m, 2H), 3.21–3.62 (m, 3H), 3.80 and 3.82 (s, s, 3H), 4.14 and 4.25 (s, s, 1H), 4.31 (q, 2H, J=7.0 Hz), 6.22 (m, 1H), 7.50 (s, 1H).

Anal. calc'd for C$_{16}$H$_{21}$NO$_5$S$_2$: C, 51.73; H, 5.70; N, 3.77; S, 17.26. Found: C, 51.65; H, 5.72; N, 3.73; S, 17.15.

(k) Preparation of 6-[2-(5-Ethoxycarbonyl-3-methyl-thiopen-2-yl)-ethyl]-3(R)-methoxy-5,6-dihydro-2H-[1,4]thiazine-2-carboxylic acid methyl ester (41)

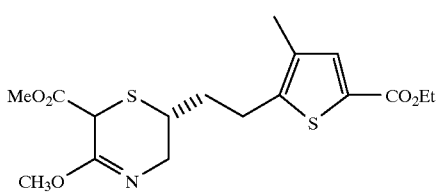

41

Starting with lactam (40), compound (41) was prepared in quantitative crude yield according to the general procedure described for compound (11) and was used without further purification.

(l) Preparation of 5-[2-(2-Amino-4-oxo-4,6,7,8-tetrahydro-3H-pyrimido[5,4-b]thiazin-6(R)-yl)-ethyl]-4-methyl-thiophene-2-carboxylic acid ethyl ester (42)

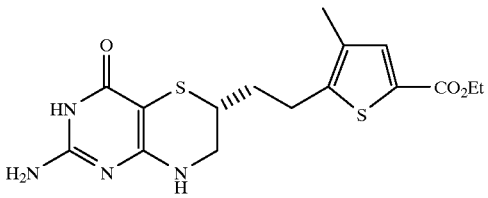

42

Starting with lactim ether (41), compound (42) was prepared in 27% yield according to the general procedure described for compound (12). (m.p. 120–140° C. with decomp.).

[α]$_{589}$ +57.1° (c=0.67, DMSO).

IR (KBr) 3337, 2926, 1701, 1653, 1635, 1599, 1449, 1250, 1072 cm$^{-1}$.

$^1$H NMR (DMSO-d$_6$) δ: 1.22 (t, 3H, J=7.0 Hz), 1.60–1.75 (m, 1H), 1.80–1.92 (m, 1H), 2.10 (s, 3H), 2.86 (m, 2H), 3.12–3.52 (m, 3H), 4.20 (q, 2H, J=7.0 Hz), 6.02 (s, 2H), 6.65 (s, 1H), 7.50 (s, 1H), 10.08 (s, 1H).

Anal. calc'd for C$_{16}$H$_{20}$N$_4$O$_3$S$_2$.0.8 H$_2$O: C, 48.66; H, 5.51; N, 14.19; S, 16.24. Found: C, 48.77; H, 5.58; N, 14.07; S, 16.16.

HRMS calc'd for C$_{16}$H$_{20}$N$_4$O$_3$S$_2$: (M+H+) 381.1055. Found: 381.1067.

(m) Preparation of 5-[2-(2-Amino-4-oxo-4,6,7,8-tetrahydro-3H-pyrimido[5,4-b][1,4]thiazin-6(R)-yl)-ethyl]-4-methyl-thiophone-2-carboxylic acid (43)

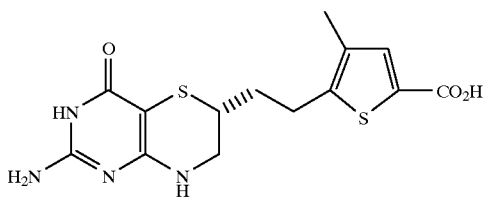

43

Starting with ester (42), compound (43) was prepared in 92% yield according to the general procedure described for compound (13). (m.p. 253° C., with decomp.)

$[\alpha]_{589}$ +60.7° (c=0.29, 1N NaOH).

IR (KBr) 3339 (broad), 2922, 1641, 1539, 1451, 1346, 1269 cm$^{-1}$.

$^1$H NMR (DMSO-d$_6$) δ: 1.64 (m, 1H), 1.82 (m, 1H), 2.09 (s, 3H), 2.78–2.94 (m, 2H), 3.10–3.55 (m, 3H—partially obscured by H$_2$O), 6.10 (s, 2H), 6.69 (s, 1H), 7.42 (s, 1H), 10.15 (s, 1H), 12.75 (br s, 1H).

HRMS calc'd for C$_{14}$H$_{16}$N$_4$O$_3$S$_2$: (M+Na+) 375.0562. Found: 375.0575.

(n) Preparation of 5-{2-[2-(2-Amino-4-oxo-4,6,7,8-tetrahydro-3H-pyrimido[5,4-b][1,4]thiazin-6(R)-yl)-ethyl]-4-methyl-thiophone}-2-L-glutamic acid diethyl ester (44)

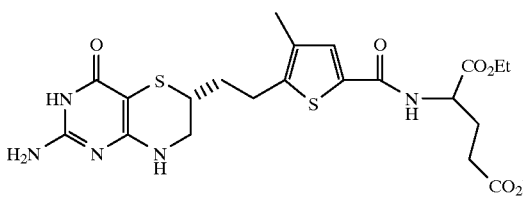

44

Starting with acid (43), compound (44) was prepared in 71% yield according to the general procedure described for compound (15). (m.p. 124° C. with foaming).

$[\alpha]_{589}$ +33.6° (c=0.50, DMSO).

IR (KBr) 2996, 2860, 1734, 1653, 1636, 1559, 1456, 1206 cm$^{-1}$.

$^1$H NMR (DMSO-d$_6$) δ: 1.11 (t, 3H, J=7.0 Hz), 1.15 (t, 3H, J=7.0 Hz), 1.75–2.04 (m, 4H), 2.10 (s, 3H), 2.37 (t, 2H, J=7.4 Hz), 2.85 (m, 2H), 3.12 (m, 2H), 3.50 (m, 1H), 4.00 (q, 2H, J=7.0 Hz), 4.06 (q, 2H, J=7.0 Hz), 4.31 (m, 1H), 6.01 (s, 2H), 6.65 (s, 1H), 7.55 (s, 1H), 8.53 (d, 1H, J=7.7 Hz), 10.08 (s, 1H).

HRMS calc'd for C$_{23}$H$_{31}$N$_5$O$_6$S$_2$: (M+Cs+) 670.0770. Found: 670.0742.

(o) Preparation of 5-{2-[2-(2-Amino-4-oxo-4,6,7,8-tetrahydro-3H-pyrimido[5,4-b][1,4]thiaizin-6(R)-yl)-ethyl]-4-methyl-thiophene}-2-L-glutamic acid (45)

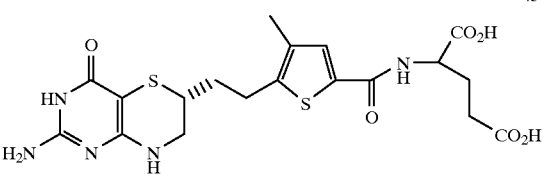

45

Starting with diester (44), compound (45) was prepared in 77% yield according to the general procedure described for compound (15). (m.p. 210° C. with decomp.).

$[\alpha]_{589}$ +64.4° (c=0.45, 1N NaOH).

IR (KBr) 3341 (broad), 2928, 1701, 1638, 1536, 1449, 1340 cm$^{-1}$.

$^1$H NMR (DMSO-d$_6$) δ: 1.78–2.05 (m, 4H), 2.10 (s, 3H), 2.28 (t, 2H, J=7.0 Hz), 2.82 (m, 2H), 3.45 (m, 3H—partially obscured by H$_2$O), 4.25 (m, 1H), 5.98 (s, 2H), 6.65 (s, 1H), 7.54 (s, 1H), 8.38 (d, 1H, J=7.7 Hz), 10.05 (s, 1H), 12.5 (br s, 2H).

Anal. calc'd for C$_{19}$H$_{23}$N$_5$O$_6$S.0.7 H$_2$O: C, 46.18; H, 4.98; N, 14.17; S, 12.98. Found: C, 46.13; H, 4.99; N, 14.09; S, 13.02.

EXAMPLE 4

Preparation of N-(5-[2-(2-Amino-4(3H)-oxo-5,6,7,8-tetrahydropyrimido[5,6-b][1,4]thiazin-6(S)-yl) ethyl]-4-methyltheno-2-yl)-L-glutamic acid (64)

(a) Preparation of 5-[2,2-Dimethyl-1,3-dioxolan-4(R)-yl-ethynyl]-4-methylthiophene-2-carboxylic acid ethyl ester (46)

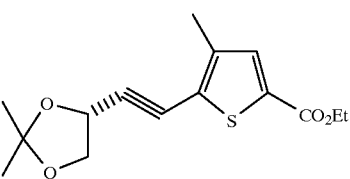

46

Starting with 2,2-dimethyl-4(R)-ethynyl-1,3-dioxolane and 5-bromo-4-methylthiophene-2-carboxylic acid ethyl ester, compound (46) was prepared in 57% yield according to the general procedure described for compound (1).

$[\alpha]_{589}$ –38.3° (c=0.95, CH$_3$OH).

$^1$H NMR (CDCl$_3$) δ: 1.36 (t, 3H, J=7.0 Hz), 1.42 (s, 3H), 1.53 (s, 3H), 2.29 (s, 3H), 4.04 (dd, 1H, J=6.3, 8.1 Hz), 4.26 (dd, 1H, J=6.3, 8.1 Hz), 4.32 (q, 2H, J=7.0 Hz), 4.99 (t, 1H, J=6.3 Hz), 7.50 (s, 1H).

Anal. calc'd for C$_{15}$H$_{18}$O$_4$S: C, 61.20; H, 6.16; S, 10.89. Found: C, 61.33; H, 6.20; S, 10.80.

(b) Preparation of 5-(2-[2,2-Dimethyl-1,3-dioxolan-4(R)-yl-ethyl)-4-methylthiophene-2-carboxylic acid ethyl ester (47)

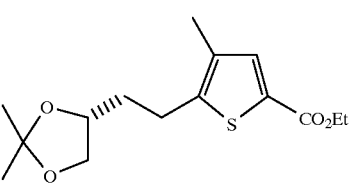

47

Starting with alkyne (46), compound (47) was prepared in 96% yield according to the general procedure described for compound (2).

$[\alpha]_{589}$ +13.4° (c=0.72, CH$_3$OH).

$^1$H NMR (CDCl$_3$) δ=1.35 (t, 3H, J=7.2 Hz), 1.36 (s, 3H), 1.43 (s, 3H), 1.79–1.99 (m, 2H), 2.16 (s, 3H), 2.75–2.96 (m, 2H), 3.55 (dd, 1H, J=7.0, 7.7 Hz), 4.04 (dd, 1H, J=5.9, 7.7 Hz), 4.08–4.16 (m, 1H), 4.33 (q, 2H, J=7.2 Hz), 7.50 (s, 1H).

Anal. calc'd for C$_{15}$H$_{22}$O$_4$S: C, 60.38; H, 7.43; s, 10.74. Found: C, 60.48; H, 7.40; S, 10.69.

(c) Preparation of 5-[3(R),4-Dihydroxybutyl]-4-methylthiophene-2-carboxylic acid ethyl ester (48)

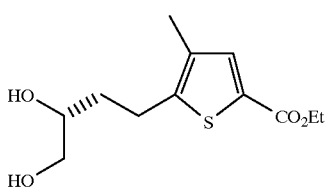

48

Starting with dioxolane (47), compound (48) was prepared in 89% yield according to the general procedure described for compound (3).

[α]₅₈₉ +25.4° (c=0.82, CH₃OH).
¹H NMR (CDCl₃) δ=1.35 (t, 3H, J=7.0 Hz), 1.73–1.81 (m, 2H), 2.17 (s, 3H), 2.80–3.00 (m, 2H), 3.48 (dd, 1H, J=7.5, 10.8 Hz), 3.68 (dd, 1H, J=3.1, 10.8 Hz), 3.71–3.79 (m, 1H), 4.31 (q, 2H, J=7.0 Hz), 7.50 (s, 1H).
Anal. calc'd for $C_{12}H_{18}O_4S$: C, 55.79; H, 7.02; S, 12.41 Found: C, 55.69; H, 7.03; S, 12.48.

(d) Preparation of 5-[3(R)-Hydroxy-4-(p-toluenesulfonyloxy)-butyl]-4-methylthiophene-2-carboxylic acid ethyl ester (49)

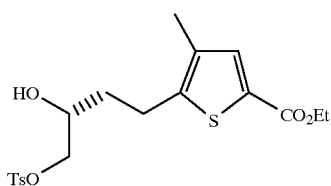

49

Starting with diol (48), compound (49) was prepared in 65% yield according to the general procedure described for compound (4).

[α]₅₈₉ +7.5° (c=0.59, CH₃OH).
¹H NMR (CDCl₃) δ=1.35 (t, 3H, J=7.0 Hz), 1.68–1.79 (m, 2H), 2.13 (s, 3H), 2.46 (s, 3H), 2.78–2.95 (m, 2H), 3.82–3.94 (m, 2H), 4.03 (dd, 1H, J=1.8, 8.8 Hz), 4.31 (q, 2H, J=7.0 Hz), 7.36 (d, 2H, J=8.1 Hz), 7.48 (s, 1H), 7.79 (d, 2H, J=8.1 Hz)
Anal. calc'd for $C_{19}H_{24}O_6S_2$: C, 55.32; H, 5.86; S, 15.54. Found: C, 55.26; H, 5.87; S, 15.64.

(e) Preparation of 5-[4-(tert-Butyldimethylsilyloxy)-3(S)-hydroxybutyl]-4-methylthiophene-2-carboxylic acid ethyl ester (50)

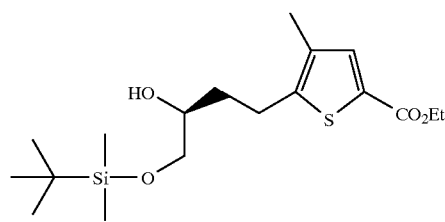

50

Starting with diol (33), compound (50) was prepared in 95% yield according to the general procedure described for compound (16).

[α]₅₈₉ −23.5° (c=1.19, CH₃OH).
¹H NMR (CDCl₃) δ: 0.07 (s, 6H), 0.90 (s, 9H), 1.35 (t, 3H, J=7.1 Hz), 1.61–1.81 (m, 2H), 2.17 (s, 3H), 2.79–3.01 (m, 2H), 3.43 (dd, 1H, J=7.0,9.6 Hz), 3.63 (dd, 1H, J=3.3, 9.6 Hz), 3.66–3.71 (m, 1H), 4.31 (q, 2H, J=7.1 Hz), 7.50 (s, 1H).

Anal. calc'd for $C_{18}H_{32}O_4SSi$: C, 58.03; H, 8.66; S, 8.60. Found: C, 57.71; H, 9.14; S, 8.47.

(f) Preparation of 5-[4-(tert-Butyldimethylsilyloxy)-3(S)-(methanesulfonyloxy)butyl]-4-methylthiophene-2-carboxylic acid ethyl ester (51)

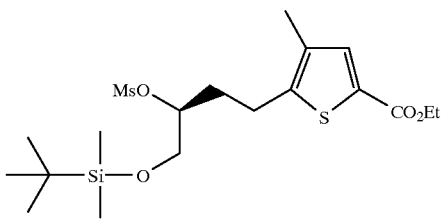

51

Starting with alcohol (50), compound (51) was prepared in 84% yield according to the general procedure described for compound (17).

[α]₅₈₉ +3.9° (c=1.48, CH₃OH).
¹H NMR (CDCl₃) δ: 0.09 (s, 6H), 0.90 (s, 9H), 1.35 (t, 3H, J=7.0 Hz), 1.97–2.05 (m, 2H), 2.16 (s, 3H), 2.82–3.01 (m, 2H), 3.07 (s, 3H), 3.68–3.82 (m, 2H), 4.31 (q, 2H, J=7.0 Hz), 4.69–4.77 (m, 1H), 7.50 (s, 1H).
Anal. calc'd for $C_{19}H_{34}O_6S_2Si$: C, 50.64; H, 7.60; S, 14.23. Found: C, 50.54; H, 7.58; S, 14.30.

(g) Preparation of 5-[4-Hydroxy-3(S)-(methanesulfonyloxy)butyl]-4-methylthiophene-2-carboxylic acid ethyl ester (52)

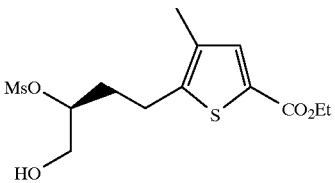

52

Starting with silyl ether (51), compound (52) was prepared in 39% yield according to the general procedure described for compound (18).

[α]₅₈₉ +14.2° (c=0.97, CH₃OH).
¹H NMR (CDCl₃) δ: 1.35 (t, 3H, J=7.0 Hz), 1.96–2.12 (m, 2H), 2.17 (s, 3H), 2.85–2.94 (m, 2H), 3.12 (s, 3H), 3.77 (dd, 1H, J=6.6, 12.5 Hz), 3.86 (dd, 1H, J=2.9, 12.5 Hz), 4.31 (q, 2H, J=7.0 Hz), 4.78–4.87 (m, 1H), 7.50 (s, 1H).
Anal. calc'd for $C_{13}H_{20}O_6S_2$: C, 46.41; H, 5.99; S, 19.06. Found: C, 46.51; H, 6.04; S, 18.95.

(h) Preparation of 5-[3(R),4-Epoxybutyl]-4-methylthiophene-2-carboxylic acid ethyl ester (53)

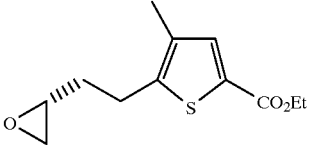

53

Starting with mesylate (52), compound (53) was prepared in 70% yield according to the general procedure described for compound (19).

[α]₅₈₉ +23.5° (c=0.80, CH₃OH).
¹H NMR (CDCl₃) δ=1.35 (t, 3H, J=7.1 Hz), 1.74–1.86 (m, 1H), 1.89–2.01 (m, 1H), 2.17 (s, 3H), 2.51 (dd, 1H, J=2.6, 14.8 Hz), 2.78 (dd, 1H, J=4.0, 14.8 Hz), 2.86–3.00 (m, 3H), 4.31 (q, 2H, J=7.1 Hz), 7.50 (s, 1H).

Anal. calc'd for $C_{12}H_{16}O_3S$: C, 59.98; H, 6.71; S, 13.34. Found: C, 59.90; H, 6.73; S, 13.41.

(i) Preparation of 5-[4-Azido-3(R)-hydroxybutyl]-4-methylthiophene-2-carboxylic acid ethyl ester (54)

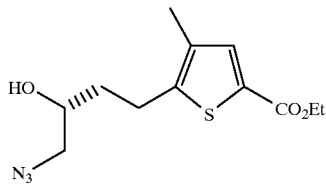

54

Starting with tosylate (49), compound (54) was prepared in 91% yield according to the general procedure described for compound (5).

Starting with epoxide (53), compound (54) was prepared in 79% yield according to the general procedure described for compound (20).

$[\alpha]_{589}$ +11.0° (c=0.58, $CH_3OH$).

$^1H$ NMR ($CDCl_3$) δ: 1.35 (t, 3H, J=7.2 Hz), 1.75–1.84 (m, 2H), 2.17 (s, 3H), 2.80–3.00 (m, 2H), 3.29 (dd, 1H, J=7.0, 12.3 Hz), 3.42 (dd, 1H, J=3.1, 12.3 Hz), 3.75–3.83 (m, 1H), 4.31 (q, 2H, J=7.2 Hz), 7.50 (s, 1H).

Anal. calc'd for $C_{12}H_{17}N_3O_3S$: C, 50.87; H, 6.05; N, 14.83; S, 11.31. Found: C, 50.94 H, 6.07; N, 14.75; S, 11.22.

(j) Preparation of 5-[4-(tert-Butoxycarbonylamino)-3(R)-hydroxybutyl]-4-methylthiophene-2-carboxylic acid ethyl ester (55)

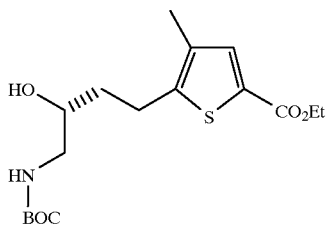

55

Starting with azide (54), compound (55) was prepared in 96% yield according to the general procedure described for compound (6).

$[\alpha]_{589}$ +22.6° (c=0.66, $CH_3OH$).

$^1H$ NMR ($CDCl_3$) δ: 1.35 (t, 3H, J=7.2 Hz), 1.45 (s, 9H), 1.72–1.81 (m, 2H), 2.16 (s, 3H), 2.78–2.99 (m, 2H), 3.09 (dd, 1H, J=7.4, 14.3 Hz), 3.29 (dd, 1H, J=2.9, 14.3 Hz), 3.70–3.78 (m, 1H), 4.31 (q, 2H, J=7.2 Hz), 7.50 (s, 1H).

Anal. calc'd for $C_{17}H_{27}NO_5S$: C, 57.12; H, 7.61; N, 3.92; S, 8.97. Found: C, 57.05 H, 7.63; N, 3.84; S, 9.07.

(k) Preparation of 5-[4-(tert-Butoxycarbonylamino)-3(R)-methanesulfonyloxy)butyl]-4-methylthiophene-2-carboxylic acid ethyl ester (56)

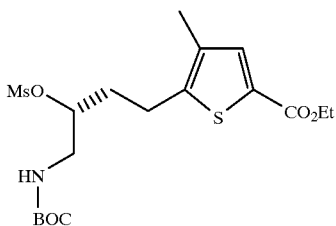

56

Starting with alcohol (55), compound (56) was prepared in 93% yield according to the general procedure described for compound (7).

$[\alpha]_{589}$ 7.8° (c=0.98, $CH_3OH$).

$^1H$ NMR ($CDCl_3$) δ: 1.35 (t, 3H, J=7.2 Hz), 1.45 (s, 9H), 1.98–2.06 (m, 2H), 2.16 (s, 3H), 2.86–2.92 (m, 2H), 3.06 (s, 3H), 3.34–3.43 (m, 2H), 4.31 (q, 2H, J=7.2 Hz), 4.77–4.84 (m, 1H), 4.92 (broad, 1H), 7.50 (s, 1H).

Anal. calc'd for $C_{18}H_{29}NO_7S$—: C, 49.64; H, 6.71; N, 3.22; S, 14.72. Found: C, 49.57; H, 6.78; N, 3.28; S, 14.70.

(l) Preparation of 5-[4-(tert-Butoxycarbonylamino)-3(S)-(acetylthio)butyl]-4-methylthiophene-2-carboxylic acid ethyl ester (57)

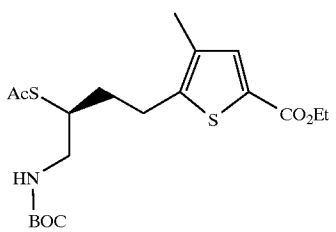

57

Starting with mesylate (56), compound (57) was prepared in 92% yield according to the general procedure described for compound (8).

$[\alpha]_{589}$ +2.8° (c=0.93, $CH_3OH$).

$^1H$ NMR ($CDCl_3$) δ: 1.34 (t, 3H, J=7.0 Hz), 1.44 (s, 9H), 1.78–1.89 (m, 1H), 1.93–2.04 (m, 1H), 2.13 (s, 3H), 2.37 (s, 3H), 2.75–2.94 (m, 2H), 3.26–3.45 (m, 2H), 3.56–3.64 (m, 1H), 4.30 (q, 2H, J=7.0 Hz), 4.75 (broad, 1H), 7.48 (s, 1H).

Anal. calc'd for $C_{19}H_{29}NO_5S_2$: C, 54.92; H, 7.03; N, 3.37; S, 15.43. Found: C, 54.81; H, 7.09; N, 3.43; S, 15.41.

(m) Preparation of 2-([1-(tert-Buoxycarbonylamino)-4-)-5-ethoxycarbonyl-3-methylthien-2-yl)but-2(S)-yl]thio)malonic acid diethyl ester (58)

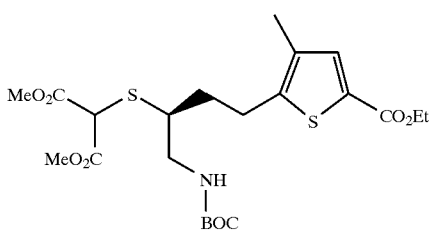

58

Starting with thioacetate (57), compound (58) was prepared in 88% yield according to the general procedure described for compound (24).

$[\alpha]_{589}$ −23.7° (c=0.68, $CH_3OH$).

$^1H$ NMR ($CDCl_3$) δ: 1.34 (t, 3H, J=7.1 Hz), 1.44 (s, 9H), 1.75–1.86 (m, 4), 1.90–1.99 (m, 1H), 2.15 (s, 3H), 2.85–2.97

(m, 2H), 3.00–3.07 (m, 1H), 3.23–3.39 (m, 2H), 3.80 (s, 6H), 3.87 (s, 1H), 4.31 (q, 2H, J=7.1 Hz), 5.12 (broad, 1H), 7.49 (s, 1H)

Anal. calc'd for $C_{22}H_{33}NO_8S_2$: C, 52.47; H, 6.60; N, 2.78; S, 12.73. Found: C, 52.49; H, 6.64; N, 2.77; S, 12.64.

(n) Preparation of 6(S)-[2-(5-ethoxycarbonyl-3-methylthien-2-yl)-ethyl-3-oxo-1,4-thiazine-2-carboxylic acid methyl ester (59)

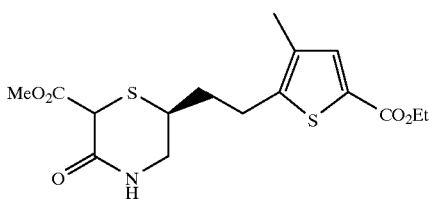

Starting with malonate (58), compound (59) was prepared in 88% yield according to the general procedure described for compound (10).

$[\alpha]_{589}$ 26.2° (c=0.81, $CH_3OH$).

$^1$H NMR ($CDCl_3$) δ: 1.35 (t, 3H, J=7.1 Hz), 1.83–2.03 (m, 2H), 2.16 (s, 3H), 2.83–2.97 (m, 2H), 3.39–3.67 (m, 3H), 3.80,3.82 (s, 3H), 4.14,4.25 (s, 1H), 4.31 (q, 2H, J=7.1 Hz), 6.29 (broad, 1H), 7.50 (s, 1H).

Anal. calc'd for $C_{144}H_{21}NO_5S2$: C, 51.73; H, 5.70; N, 3.79; S, 17.26. Found: C, 51.56; H, 5.80; N, 3.70; S, 17.09.

(o) Preparation of 6(S)-[2-(5-Ethoxycarbonyl-3-methylthien-2-yl)ethyl]-3-methoxy-1,4-thiazine-2-carboxylic acid methyl ester (60)

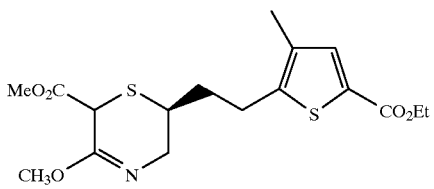

Starting with lactam (59), compound (60) was prepared in quantitative crude yield according to the general procedure described for compound (11) and was used without further purification.

(p) Preparation of 5-[2-(2-Amino-4(3H)-oxo-5,6,7,8-tetrahydro-pyrimido[5,6-b][1,4]thiazin-6(S)-yl)ethyl]-4-methylthiophene-2-carboxylic acid ethyl ester (61)

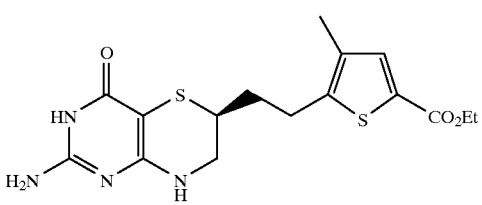

Starting with imidoether (60), compound (61) was prepared in 27% yield according to the general procedure described for compound (12).

$[\alpha]_{589}$ 41.5° (c=0.66, DMSO).

$^1$H NMR (DMSO-$d_6$) δ: 1.25 (t, 3H, J=7.0 Hz), 1.62–1.73 (m, 1H), 1.80–1.91 (m, 1H), 2.13 (s, 3H), 2.79–2.97 (m, 3H), 3.19–3.26 (m, 1H), 3.47–3.55 (m, 1H), 4.22 (q, 2H, J=7.0 Hz), 6.05 (s, 2H), 6.68 (s, 1H), 7.53 (s, 1H), 10.10 (s, 1H).

(q) Preparation of 5-[2-(2-Amino-4(3H)-oxo-5,6,7,8-tetrahydro-pyrimido[5,6-b][1,4]thiazin-6(S)-yl)ethyl]-4-methylthiophene-2-carboxylic acid (62)

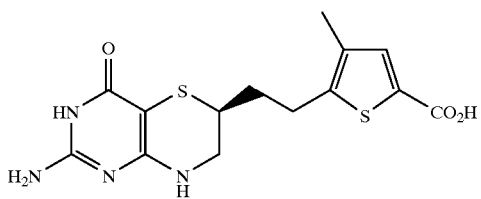

Starting with ester (61), compound (62) was prepared in 77% yield according to the general procedure described for compound (13).

$[\alpha]_{589}$ 77.9° (c=0.58, 1N NaOH).

$^1$H NMR (DMSO-$d_6$) δ: 1.62–1.73 (m, 1H), 1.79–1.92 (m, 1H), 2.12 (s, 3H), 2.81–2.98 (m, 3H), 3.16–3.26 (m, 1H), 3.50–3.58 (m, 1H), 6.21 (br s, 2H), 6.76 (br s, 1H), 7.45 (s, 1H), 10.24 (broad, 1H), 12.76 (broad, 1H).

Anal. calc'd for $C_{14}H_{16}N_4O_3S_2 \cdot 1.4\ H_2O$: C, 44.52; H, 5.02; N, 14.845,16.98. Found: C, 44.60; H, 4.86; N, 14.70; S, 16.92.

(r) Preparation of N-(5-[2-(2-Amino-4(3H)-oxo-5,6,7,8-tetrahydropyrimido[5,6-b][1,4]thiazin-6(S)-yl)ethyl]-4-methyltheno-2-yl)-L-glutamic acid diethyl ester (63)

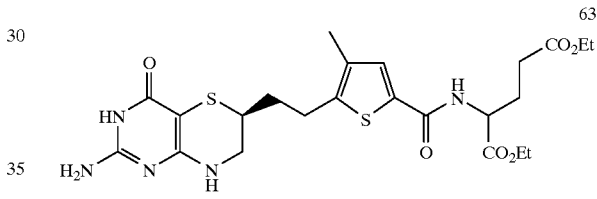

Starting with acid (62), compound (63) was prepared in 60% yield according to the general procedure described for compound (14).

$[\alpha]_{589}$ –54.1° (c=0.61, DMSO).

$^1$H NMR (DMSO-$d_6$) δ: 1.15 (t, 3H, J=7.1 Hz), 1.17 (t, 3H, J=7.1 Hz), 1.61–1.72 (m, 1H), 1.77–2.07 (m, 3H), 2.13 (s, 3H), 2.40 (t, 2H, J=7.5 Hz), 2.77–2.94 (m, 3H), 3.18–3.28 (m, 1H), 3.50–3.56 (m, 1H), 4.03 (q, 2H, J=7.1 Hz), 4.08 (q, 2H, J=7.1 Hz), 4.34 (ddd, 1H, J=5.4, 7.7, 9.6 Hz), 6.02 (s, 2H), 6.67 (s, 1H), 7.58 (s, 1H), 8.55 (d, 1H, J=7.7 Hz), 10.06 (s, 1H).

Anal. calc'd for $C_{23}H_{31}N_5O_6S_2 \cdot 0.5H_2O$: C, 50.53; H, 5.90; N, 12.81 S, 11.73. Found: C, 50.56; H, 5.92; N, 12.67; S, 11.54.

(s) Preparation of N-(5-[2-(2-Amino-4(3H)-oxo-5,6,7,8-tetrahydropyrimido[5,6-b][1,4]thiazin-6(S)-yl)ethyl]-4-methyltheno-2-yl)-L-glutamic acid (64)

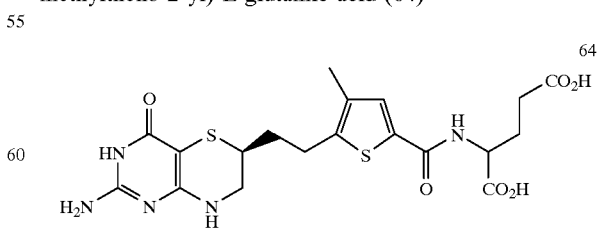

Starting with diester (63), compound (64) was prepared in 85% yield according to the general procedure described for compound (15).

$[\alpha]_{589}$ 36.8° (c=0.57, 1N NaOH).

$^1$H NMR (DMSO-$d_6$) δ: 1.61–1.72 (m, 1H), 1.76–1.92 (m, 2H), 1.99–2.08 (m, 1H), 2.12 (s, 3H), 2.31 (t, 2H, J=7.0 Hz), 2.79–2.94 (m, 3H), 3.17–3.28 (m, 1H), 3.49–3.56 (m, 1H), 4.30 (ddd, 1H, J=5.7, 7.7, 9.8 Hz), 6.08 (s, 2H), 6.70 (s, 1H), 7.58 (s, 1H), 8.44 (d, 1H, J=7.7 Hz), 10.12 (br s, 1H), 12.43 (broad, 2H).

Anal. calc'd for $C_{19}H_{23}N_5O_6S_2 \cdot 0.75\, H_2O$: C, 46.09; H, 4.99; N, 14.15; S, 12.95. Found: C, 46.09; H, 4.98; N, 14.01; S, 12.77.

We claim:

1. A method of making a compound of the formula

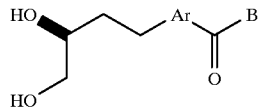

VII or its enantiomer, wherein Ar is a substituted or unsubstituted five- or six-membered aromatic group and B is either an amino acid linked through the amino portion to form an amide or a $C_1$–$C_6$ alcohol linked through the alcohol portion to form an ester, comprising the steps of:

(a) reacting a compound of the formula

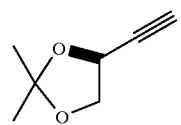

III or its enantiomer

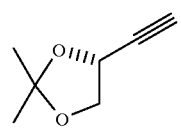

XVII with a compound of the formula

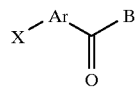

IV wherein X is bromo, fluoro, chloro or iodo, and B and Ar are as defined above, to form a compound of the formula

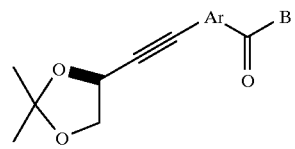

V or its enantiomer, wherein Ar and B are as defined above;

(b) reacting the compound of formula V or its enantiomer with a reducing agent to obtain a compound of the formula

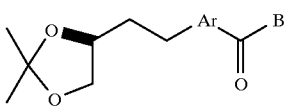

VI or its enantiomer, wherein Ar and B are as defined above; and (c) reacting the compound of the formula VI or its enantiomer with an acid to obtain the compound of the formula VII or its enantiomer.

2. A method according to claim 1, wherein in step (a) the reacting is carried out in the presence of (i) a transition-metal catalyst containing one or more metals selected from the group consisting of palladium, copper and nickel, and (ii) a non-nucleophilic auxiliary base (iii) in a solvent in which at least one of the reactant compounds is at least partially soluble.

3. A method according to claim 1, wherein in step (b) the reducing agent is hydrogen gas in the presence of a metal catalyst containing palladium or platinum.

4. A method according to claim 1, wherein in step (c) the acid is p-toluenesulfonic acid.monohydrate and the reacting is carried out in methanol or ethanol.

5. A method according to claim 1, wherein in step (a), a compound of the formula III is reacted.

6. A method according to claim 1, wherein in step (a), a compound of the formula XVII is reacted.

7. A method of preparing a compound of the formula

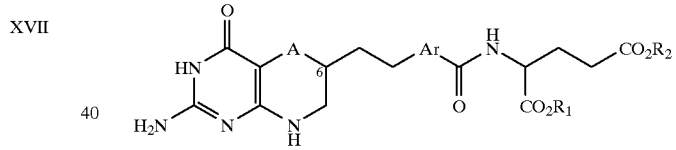

wherein A is an oxygen, sulfur or selenium atom, Ar is a substituted or unsubstituted five- or six-membered aromatic group, and $R_1$ and $R_2$ are independently a hydrogen atom or a moiety that forms together with the attached $CO_2$ a readily hydrolyzable ester group, comprising:

reacting a compound of the formula

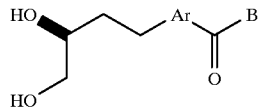

VII or its enantiomer, wherein Ar is a substituted or unsubstituted five- or six-membered aromatic group and B is either an amino acid linked through the amino portion to form an amide or a $C_1$–$C_6$ alcohol linked through the alcohol portion to form an ester, to form the compound of the formula I that is optically pure.

8. A method according to claim 7, wherein the compound of the formula VII is prepared by steps comprising:

(a) reacting a compound of the formula

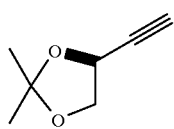  III or its enantiomer

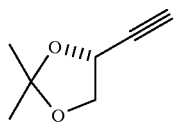

with a compound of the formula

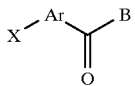  IV wherein X is bromo, fluoro, chloro or iodo, and B and Ar are as defined above,
to form a compound of the formula

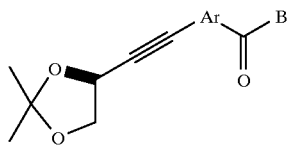  V or its enantiomer, wherein Ar and B are as defined above;

(b) reacting the compound of formula V or its enantiomer with hydrogen gas in the presence of a metal catalyst to obtain a compound of the formula

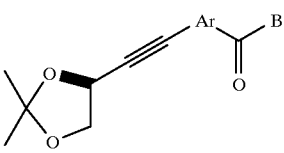  V or its enantiomer, wherein Ar and B are as defined above; and (c) reacting the compound of the formula VI or its enantiomer with an acid in an alcoholic solvent to obtain the compound of the formula VII or its enantiomer.

9. A method according to claim 8, wherein in step (a) the reacting is carried out in the presence of (i) a transition-metal catalyst containing one or more metals selected from the group consisting of palladium, copper and nickel, and (ii) a non-nucleophilic auxiliary base (iii) in a solvent in which at least one of the reactant compounds is at least partially soluble.

10. A method according to claim 7, wherein Ar is a 5-membered aromatic group having a sulfur ring atom.

11. A method according to claim 7, wherein the compound of the formula I has the (R) configuration.

12. A method according to claim 7, wherein the compound of the formula I has the (S) configuration.

13. A method according to claim 7, wherein the compound of the formula VII or its enantiomer is 5-(3(S)-4-dihydroxy-butyl)-thiophene-2-carboxylic acid ethyl ester.

* * * * *

UNITED STATES PATENT AND TRADEMARK OFFICE
CERTIFICATE OF CORRECTION

PATENT NO. : 5,981,748
DATED : November 9, 1999
INVENTOR(S) : Michael D. Varney et al.

It is certified that error appears in the above-identified patent and that said Letters Patent is hereby corrected as shown below:

Title Page
[75] INVENTORS
"Calsbad" should read --Carlsbad--.

Title Page
[56] REFERENCES CITED FOREIGN PATENT DOCUMENTS
"2678377    5/1988    European Pat. Off." should read
--268377    5/1988    European Pat. Off.--

OTHER PUBLICATIONS
After "morrison ... of": "Enzyme-atalysed" should read --Enzyme-Catalysed--.

Column 1
Line 32, "inhibitor" should read --inhibitory--.

Column 2
Line 11, 97.5t" should read --97,5%--.

Column 3
Line 1, "for a" should read --for B--.

Column 5
Line 8, "R2" should read --$R_2$--;
Line 53, "formula I The" should read --formula I. ¶ The--.

Column 9
Line 58, "she" should read --the--.

Column 12
Line 25, "enter (1)" should read --ester (1)--;
Line 53, "MeOH." should read --MeOH).--

Column 13
Line 29, "-thiophone-2-" should read --thiophene-2— --.

Column 15
Line 58, "120 msol)" should read --(120 mmol)--.

UNITED STATES PATENT AND TRADEMARK OFFICE
CERTIFICATE OF CORRECTION

PATENT NO.   : 5,981,748
DATED        : November 9, 1999
INVENTOR(S)  : Michael D. Varney et al.

It is certified that error appears in the above-identified patent and that said Letters Patent is hereby corrected as shown below:

Column 18
Line 35, "$C_{15}H_4NO_5S_2$:" should read $C_{15}H_{19}NO_5S_2$:--;
Line 58, "-The" should read --The--.

Column 19
Line 63, "$H_2O$)," should read --$H_2O$),--.

Column 22
Line 47, "(d 1H," should read --(d, 1H,--.

Column 23
Line 40, "1283 1262," should read -- 1283, 1262,--.

Column 25
Line 65, (5-Buthoxycarbonyl-" should read (5-Butoxycarbonyl- --.

Column 26
Line 22, (5-Buthoxycarbonyl-" should read (5-Butoxycarbonyl- --.

Column 28
Line 37, "(9, 3H)," should read --(s, 3H),--;
Line 39, "(9, 1H)." should read --(s, 1H).--.

Column 31
Line 51, (5-Buthoxycarbonyl-" should read (5-Butoxycarbonyl- --.

Column 32
Line 1, "[α]" should read --[α]$_{589}$-;
Line 67, "thiophone" should read --thiophene--.

Column 33
Line 26, "thiophone}-" should read --thiophene}-- --;
Line 53, "thiaizin-6 (R)--.

UNITED STATES PATENT AND TRADEMARK OFFICE
CERTIFICATE OF CORRECTION

PATENT NO.   : 5,981,748  
DATED        : November 9, 1999  
INVENTOR(S)  : Michael D. Varney et al.

Page 3 of 3

It is certified that error appears in the above-identified patent and that said Letters Patent is hereby corrected as shown below:

Column 34  
Line 17, "acid (64) should read --acid (46) --.

Column 38  
Line 47, "tert-Buoxycarbonylamino)" should read --(tert-Butoxycarbonylamino)--.

Column 39  
Line 26, "$C_{144}H_{21}NO_5S2$:" should read --$C_{16}H_{21}NO_5S_2$--.

Column 40  
Line 23, "16.98." should read --S, 16.98.--.

Column 44  
Line 5, should read

Signed and Sealed this

Twenty-first Day of August, 2001

*Attest:*

*Attesting Officer*

NICHOLAS P. GODICI  
*Acting Director of the United States Patent and Trademark Office*